United States Patent
Parameswaran

(10) Patent No.: US 12,023,354 B2
(45) Date of Patent: Jul. 2, 2024

(54) TARGETING B CELL ACTIVATING FACTOR RECEPTOR (BAFF-R) USING LIGAND-BASED CHIMERIC ANTIGEN RECEPTOR (CAR)-T CELLS

(71) Applicant: Case Western Reserve University, Cleveland, OH (US)

(72) Inventor: Reshmi Parameswaran, Solon, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 579 days.

(21) Appl. No.: 16/888,989

(22) Filed: Jun. 1, 2020

(65) Prior Publication Data

US 2020/0376032 A1 Dec. 3, 2020

Related U.S. Application Data

(60) Provisional application No. 62/980,727, filed on Feb. 24, 2020, provisional application No. 62/908,795, filed on Oct. 1, 2019, provisional application No. 62/855,130, filed on May 31, 2019.

(51) Int. Cl.
| | |
|---|---|
| *A61K 35/17* | (2015.01) |
| *A61K 38/17* | (2006.01) |
| *A61K 45/06* | (2006.01) |
| *A61P 35/02* | (2006.01) |
| *C07K 14/705* | (2006.01) |
| *C07K 14/725* | (2006.01) |
| *C07K 16/28* | (2006.01) |
| *A61K 39/00* | (2006.01) |

(52) U.S. Cl.
CPC ............ *A61K 35/17* (2013.01); *A61K 38/177* (2013.01); *A61K 38/1774* (2013.01); *A61K 45/06* (2013.01); *A61P 35/02* (2018.01); *C07K 14/7051* (2013.01); *C07K 14/70517* (2013.01); *C07K 14/70521* (2013.01); *C07K 14/70575* (2013.01); *C07K 14/70578* (2013.01); *C07K 16/2803* (2013.01); *A61K 2039/505* (2013.01); *C07K 2317/76* (2013.01); *C07K 2319/02* (2013.01); *C07K 2319/03* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 2008/0181888 A1 | 7/2008 | Ambrose et al. | |
| 2019/0135894 A1* | 5/2019 | Ma ................... | C07K 14/70596 |

FOREIGN PATENT DOCUMENTS

| | | | | | |
|---|---|---|---|---|---|
| WO | WO-2016210293 A1 * | 12/2016 | ............. | A61K 35/17 |
| WO | 2017214167 A1 | 12/2017 | | |
| WO | 2018/087557 A1 | 5/2018 | | |
| WO | 2018132513 A1 | 7/2018 | | |
| WO | WO-2018151836 A1 * | 8/2018 | ........... | A61K 31/192 |
| WO | 2018237022 A1 | 12/2018 | | |

OTHER PUBLICATIONS

Qin, et al.; CAR T cells targeting BAFF-R can overcome CD19 antigen loss in B cell malignancies, HHS Public Access Author manuscript; Published in final edited form as: Sci Transl. Med. Sep. 25, 2019; 11 (511): doi 10.1126-scitranslmed.aaw9414.
Vicioso, et al.; Combination Therapy for Treating Advanced Drug-Resistant Acute Lymphoblastic Leukemia; Cancer Immunology Research, 7(7) Jul. 2019 DOI: 10.1158/2326-6066; CIR-19-0058.
Wong, Derek P., et al. "A BAFF ligand-based CAR-T cell targeting three receptors and multiple B cell cancers." Nature communications 13.1 (2022): 1-17.
Turazzi, Nice, et al. "Engineered T cells towards TNFRSF13C (BAFFR): a novel strategy to efficiently target B-cell acute lymphoblastic leukaemia." British journal of haematology 182.6 (2018): 939-943.
Parameswaran, Reshmi, "Developing BAFF Car-T cells to target malignant B cells", PowerPoint Presentation, disclosure date May 1, 2019, Cleveland Ohio, pp. 1-32.
Parameswaran, Reshmi, "BAFF CAR T and NK Calls for B-Cell Malignancies and Autoimmune Diseases", Department of Pathology, Case Western Reserve University, PowerPoint Presentation, disclosure date Oct. 2-4, 2019, San Diego, California, 1 page.
United Kingdom Application No. GB2206128.7, Examination Report dated Mar. 14, 2024.

* cited by examiner

*Primary Examiner* — Sharon X Wen
(74) *Attorney, Agent, or Firm* — TAROLLI, SUNDHEIM, COVELL & TUMMINO, LLP

(57) ABSTRACT

The disclosure relates generally to ligand-based chimeric antigen receptor (CAR) cells. More specifically, the CAR cells express B-cell activating factor (BAFF) protein for recognition by a receptor of BAFF on the surface of a cell. CAR cells can include cytotoxic T lymphocytes, natural killer (NK) cells or natural killer T (NKT) cells that express a chimeric receptor that recognizes a receptor of BAFF. The disclosure further relates to methods of treating a variety of conditions, such as cancers and autoimmune diseases, using the disclosed CAR cells.

13 Claims, 9 Drawing Sheets

Specification includes a Sequence Listing.

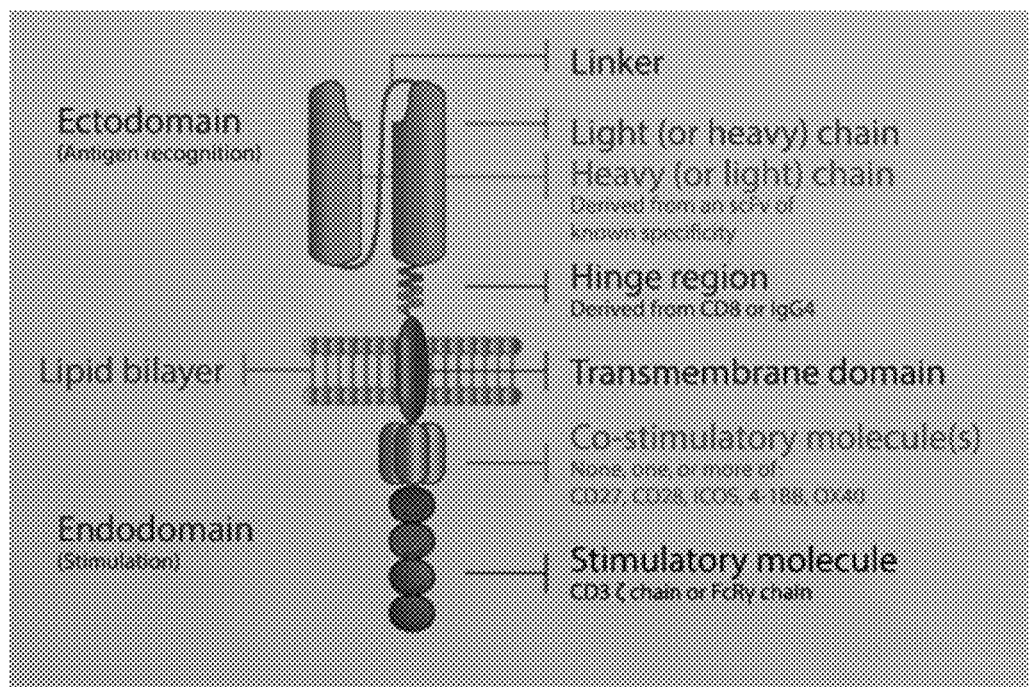
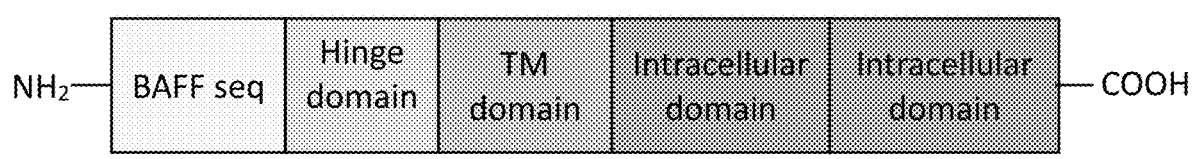
FIG. 1

FIG. 2

SEQ ID NO:15

| full-length human BAFF | CD8α hinge | CD8α TM domain | 41BB signaling domain | CD3ζ signaling domain |

SEQ ID NOs:16 & 17

| truncated human BAFF | CD8α hinge | CD8α TM domain | 41BB signaling domain | CD3ζ signaling domain |

SEQ ID NO:21

| signal peptide | full-length BAFF | IgG1 hinge | CD28 TM domain | CD28 & OX40 signaling domain | CD3ζ signaling domain |

SEQ ID NOs:22 & 23

| signal peptide | full-length BAFF | IgG1 hinge | CD28 TM domain | CD28 & OX40 signaling domain | CD3ζ signaling domain |

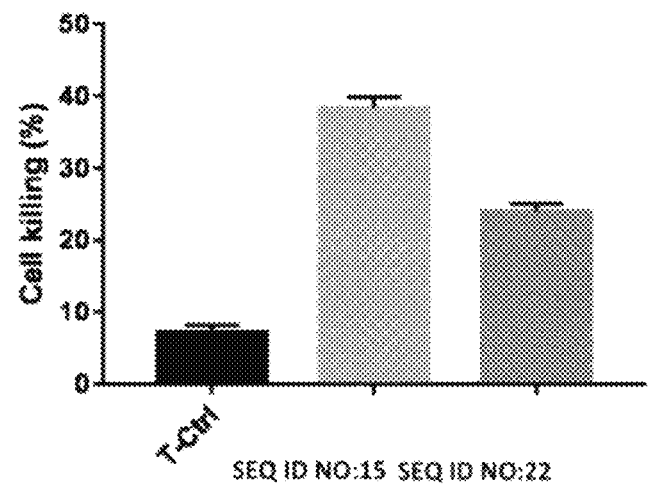
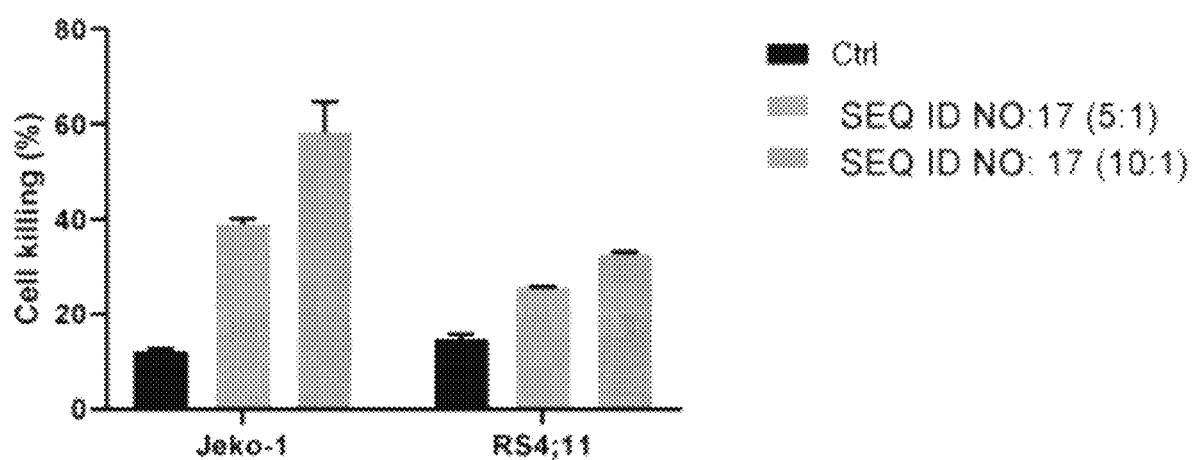
Fig. 6

TARGETING B CELL ACTIVATING FACTOR RECEPTOR (BAFF-R) USING LIGAND-BASED CHIMERIC ANTIGEN RECEPTOR (CAR)-T CELLS

RELATED APPLICATIONS

This application claims the benefit of U.S. Provisional Application No. 62/980,727 filed Feb. 24, 2020; U.S. Provisional Application No. 62/908,795 filed Oct. 1, 2019; and U.S. Provisional Application No. 62/855,130 filed May 31, 2019, all of which are hereby incorporated by reference in their entireties.

REFERENCE TO A SEQUENCE LISTING

A Sequence Listing is provided in this patent document as a txt file entitled, "60147-SEQ-LIST_ST25.txt" created May 29, 2020, with a size of 46 kB. The contents of this file are incorporated herein by reference in its entirety.

TECHNICAL FIELD

The disclosure relates generally to chimeric antigen receptor (CAR) cells that recognizes a receptor of B-cell activating factor (BAFF) on the surface of a cell. More specifically, this disclosure is related to cytotoxic T lymphocytes, natural killer (NK) cells or natural killer T (NKT) cells expressing a chimeric receptor that recognizes a receptor of BAFF. The disclosure further relates to methods of treating a variety of conditions, such as cancers and autoimmune diseases, using the disclosed CAR cells.

BACKGROUND

A number of cancers are, at present, incurable. For others, chemotherapy is only partially effective, and a significant proportion of patients relapse following treatment. Some haematological malignancies can be treated by hematopoietic stem cell transplantation (HSCT), but fewer than 30% of patients requiring HSCT have a suitable donor and are the requisite age. In another example, about 20% of Acute Lymphoblastic Leukemia (ALL) patients, the most common childhood cancer in the United States with more than 3,000 children being diagnosed each year, develop resistance to traditional chemotherapeutic approaches. Thus, there is an urgent need to develop new therapeutic routes to treat patients across a wide swath of conditions.

B-cell activating factor (BAFF) is a cytokine belonging to the tumor necrosis factor (TNF) ligand family. BAFF signaling is essential for the generation of mature B-cells and it helps survival of normal and malignant B cells. BAFF has at least three known receptors: B-cell maturation antigen transmembrane activator (BCMA), CAML interactor (TACI) and BAFF receptor (BAFF-R). BAFF-R is specific for BAFF, while BCMA and TACI share another homologous ligand, APRIL. Recent studies have shown that BAFF-R is expressed on the surface of ALL cells, thus making inhibition of BAFF a potential target for treating ALL and other conditions in which BAFF is implicated.

SUMMARY

According to the present disclosure, in a first aspect, is a method of treating a patient in need thereof comprising administering a composition comprising cytotoxic T lymphocytes, natural killer (NK) cells, or natural killer T (NKT) cells. The cytotoxic T lymphocytes, NK cells, or NKT cells express a chimeric receptor that recognizes a receptor of B-cell activating factor (BAFF). Further, the chimeric receptor comprises SEQ ID NO:1 or a partial sequence thereof, or a variant having 95% or greater sequence homology with SEQ ID NO:1 or partial sequence thereof.

In an example of the first aspect, the partial sequence comprises SEQ ID NO:2 or a variant having 95% or greater sequence homology with SEQ ID NO:2.

In another aspect of the first aspect the partial sequence comprises SEQ ID NO:3 or a variant having 95% or greater sequence homology with SEQ ID NO:3.

In yet another example of the first aspect, the chimeric receptor further comprises one or more hinge domains.

In another example of the first aspect, the hinge domain(s) is selected from the group consisting of a hinge domain of CD8α having SEQ ID NO:4 or a variant thereof having 95% or greater sequence homology with SEQ ID NO:4 and a hinge domain of IgG1 having SEQ ID NO:5 or a variant thereof having 95% or greater sequence homology with SEQ ID NO:5.

In another example of the first aspect, the chimeric receptor further comprises one or more transmembrane domains.

In another example of the first aspect, the transmembrane domain(s) is selected from the group consisting of a transmembrane domain of CD8α having SEQ ID NO:6 or a variant thereof having 95% or greater sequence homology with SEQ ID NO:6 and a transmembrane domain of CD28 having SEQ ID NO:7 or a variant thereof having 95% or greater sequence homology with SEQ ID NO:7.

In yet another example of the first aspect, the chimeric receptor further comprises one or more intracellular domains.

In another example of the first aspect, the intracellular domain(s) is selected from the group consisting of an intracellular domain of 41BB having SEQ ID NO:8 or a variant thereof having 95% or greater sequence homology with SEQ ID NO:8, an intracellular domain of CD28 having SEQ ID NO:9 or a variant thereof having 95% or greater sequence homology with SEQ ID NO:9, an intracellular domain of CD3-zeta having SEQ ID NO:10 or a variant thereof having 95% or greater sequence homology with SEQ ID NO:10 and an intracellular domain of OX40 having SEQ ID NO:11 or a variant thereof having 95% or greater sequence homology with SEQ ID NO:11.

In yet another example of the first aspect, the chimeric receptor further comprises a hinge domain, a transmembrane domain and one or more intracellular domains.

In another example of the first aspect, the wherein the chimeric receptor comprises SEQ ID NO:15 or a variant thereof having 95% or greater sequence homology with SEQ ID NO:15.

In another example of the first aspect, the chimeric receptor comprises SEQ ID NO:16 or a variant thereof having 95% or greater sequence homology with SEQ ID NO:16.

In another example of the first aspect, the chimeric receptor comprises SEQ ID NO:17 or a variant thereof having 95% or greater sequence homology with SEQ ID NO:17.

In yet another example of the first aspect, the chimeric receptor comprises SEQ ID NO:18 or a variant thereof having 95% or greater sequence homology with SEQ ID NO:18.

In another example of the first aspect, the chimeric receptor comprises SEQ ID NO:19 or a variant thereof having 95% or greater sequence homology with SEQ ID NO:19.

In another example of the first aspect, the chimeric receptor comprises SEQ ID NO:20 or a variant thereof having 95% or greater sequence homology with SEQ ID NO:20.

In another example of the first aspect, the chimeric receptor further comprises a signaling peptide.

In one example of the first aspect, the signaling peptide comprises SEQ ID NO:13 or SEQ ID NO:14, or a variant thereof having 95% or greater sequence homology with SEQ ID NO:13 or SEQ ID NO:14.

In yet another example of the first aspect, the chimeric receptor comprises SEQ ID NO:21 or a variant thereof having 95% or greater sequence homology with SEQ ID NO:21.

In another example of the first aspect, the chimeric receptor comprises SEQ ID NO:22 or a variant thereof having 95% or greater sequence homology with SEQ ID NO:22.

In another example of the first aspect, the chimeric receptor comprises SEQ ID NO:23 or a variant thereof having 95% or greater sequence homology with SEQ ID NO:23.

In yet another example of the first aspect, the T-lymphocytes, NK cells or NKT cells are isolated from a human.

In another example of the first aspect, the T-lymphocytes, NK cells or NKT are autologous.

In another example of the first aspect, the T-lymphocytes, NK cells or NKT are allogenic.

In yet another example of the first aspect, the receptor of BAFF is selected from the group consisting of B-cell maturation antigen transmembrane activator (BCMA), CAML interactor (TACT) and BAFF receptor (BAFF-R).

In another example of the first aspect, the patient in need thereof has been diagnosed with an autoimmune disorder.

In another example of the first aspect, the autoimmune disorder presents with autoimmune B cells.

In yet another example of the first aspect, the autoimmune disorder is selected from systemic lupus erythematosus, Sjogren's syndrome, narcolepsy, diabetes, pancreatitis, Crohn's disease, Celiac disease, ankylosing spondylitis, psoriasis, Grave's Disease, and rheumatoid arthritis.

In another example of the first aspect, the patient in need thereof has been diagnosed with a cancer.

In another example of the first aspect, wherein the cancer is a hematologic malignancy.

In yet another example of the first aspect, the hematologic malignancy is selected from the group consisting of acute lymphocytic leukemia, acute myeloid leukemia, chronic lymphocytic leukemia, chronic myeloid leukemia, hairy cell leukemia, diffuse large B-cell lymphoma, mantle cell lymphoma, follicular lymphoma, marginal zone lymphoma, Acute lymphoblastic leukemia, non-Hodgkin's lymphoma, Hodgkin's lymphoma, B cell malignancies, and multiple myeloma.

In another example of the first aspect, the composition is co-administered with one or more chemotherapeutic agents.

In a second aspect is a cytotoxic T lymphocyte, natural killer (NK) cell or natural killer T (NKT) cell expressing a chimeric receptor. The chimeric receptor recognizes a receptor of B-cell activating factor (BAFF), and comprises SEQ ID NO:1 or a partial sequence thereof, or a variant having 95% or greater sequence homology with SEQ ID NO:1 or partial sequence thereof.

In an example of the second aspect, the partial sequence comprises SEQ ID NO:2 or a variant having 95% or greater sequence homology with SEQ ID NO:2.

In another example of the second aspect, the partial sequence comprises SEQ ID NO:3 or a variant having 95% or greater sequence homology with SEQ ID NO:3.

In another example of the second aspect, the chimeric receptor further comprises one or more hinge domains.

In another example of the second aspect, the hinge domain(s) is selected from the group consisting of a hinge domain of CD8α having SEQ ID NO:4 or a variant thereof having 95% or greater sequence homology with SEQ ID NO:4 and a hinge domain of IgG1 having SEQ ID NO:5 or a variant thereof having 95% or greater sequence homology with SEQ ID NO:5.

In yet another example of the second aspect, the chimeric receptor further comprises one or more transmembrane domains.

In another example of the second aspect, the transmembrane domain(s) is selected from the group consisting of a transmembrane domain of CD8α having SEQ ID NO:6 or a variant thereof having 95% or greater sequence homology with SEQ ID NO:6 and a transmembrane domain of CD28 having SEQ ID NO:7 or a variant thereof having 95% or greater sequence homology with SEQ ID NO:7.

In another example of the second aspect, the chimeric receptor further comprises one or more intracellular domains.

In another example of the second aspect, the intracellular domain(s) is selected from the group consisting of an intracellular domain of 41BB having SEQ ID NO:8 or a variant thereof having 95% or greater sequence homology with SEQ ID NO:8, an intracellular domain of CD28 having SEQ ID NO:9 or a variant thereof having 95% or greater sequence homology with SEQ ID NO:9, an intracellular domain of CD3-zeta having SEQ ID NO:10 or a variant thereof having 95% or greater sequence homology with SEQ ID NO:10 and an intracellular domain of OX40 having SEQ ID NO:11 or a variant thereof having 95% or greater sequence homology with SEQ ID NO:11.

In yet another example of the second aspect, the chimeric receptor further comprises a hinge domain, a transmembrane domain and one or more intracellular domains.

In another example of the second aspect, the chimeric receptor comprises SEQ ID NO:15 or a variant thereof having 95% or greater sequence homology with SEQ ID NO:15.

In another example of the second aspect, the chimeric receptor comprises SEQ ID NO:16 or a variant thereof having 95% or greater sequence homology with SEQ ID NO:16.

In another example of the second aspect, the chimeric receptor comprises SEQ ID NO:17 or a variant thereof having 95% or greater sequence homology with SEQ ID NO:17.

In another example of the second aspect, the chimeric receptor comprises SEQ ID NO:18 or a variant thereof having 95% or greater sequence homology with SEQ ID NO:18.

In yet another example of the second aspect, the chimeric receptor comprises SEQ ID NO:19 or a variant thereof having 95% or greater sequence homology with SEQ ID NO:19.

In another example of the second aspect, the chimeric receptor comprises SEQ ID NO:20 or a variant thereof having 95% or greater sequence homology with SEQ ID NO:20.

In another example of the second aspect, the chimeric receptor further comprises a signaling peptide. In one example, the signaling peptide comprises SEQ ID NO:13 or SEQ ID NO:14, or a variant thereof having 95% or greater sequence homology with SEQ ID NO:13 or SEQ ID NO:14.

In another example of the second aspect, the chimeric receptor comprises SEQ ID NO:21 or a variant thereof having 95% or greater sequence homology with SEQ ID NO:21.

In another example of the second aspect, the chimeric receptor comprises SEQ ID NO:22 or a variant thereof having 95% or greater sequence homology with SEQ ID NO:22.

In another example of the second aspect, the chimeric receptor comprises SEQ ID NO:23 or a variant thereof having 95% or greater sequence homology with SEQ ID NO:23.

In yet another example of the second aspect, the T-lymphocytes, NK cells or NKT cells are isolated from a human.

In another example of the second aspect, the T-lymphocytes, NK cells or NKT are autologous.

In another example of the second aspect, the T-lymphocytes, NK cells or NKT are allogenic.

In yet another example of the second aspect, the receptor of BAFF is selected from the group consisting of B-cell maturation antigen transmembrane activator (BCMA), CAML interactor (TACI) and BAFF receptor (BAFF-R).

In yet another example of the second aspect, the method of treating a cancer comprising administering to a patient in need thereof a composition comprising the cytotoxic T lymphocyte, NK cell or NKT cell according to the second aspect.

In another example of the second aspect, the method of treating an autoimmune disease comprising administering to a patient in need thereof a composition comprising the cytotoxic T lymphocyte, NK cell or NKT cell according to the second aspect.

Additional features and advantages will be set forth in the detailed description which follows, and in part will be readily apparent to those skilled in the art from that description or recognized by practicing the embodiments as described herein, including the detailed description which follows, the claims, as well as the appended drawings.

It is to be understood that both the foregoing general description and the following detailed description are merely exemplary and are intended to provide an overview or framework to understanding the nature and character of the claims. The accompanying drawings are included to provide a further understanding and are incorporated in and constitute a part of this specification. The drawings illustrate one or more embodiments, and together with the description serve to explain principles and operation of the various embodiments. Directional terms as used herein—for example, up, down, right, left, front, back, top, bottom—are made only with reference to the figures as drawn and are not intended to imply absolute orientation.

BRIEF DESCRIPTION OF THE DRAWINGS

The above and other features, examples and advantages of aspects or examples of the present disclosure are better understood when the following detailed description is read with reference to the accompanying drawings, in which:

FIG. 1 is an exemplary schematic representation of a CAR construct according to the present disclosure.

FIG. 2 is a schematic representation of exemplary CAR constructs SEQ ID NOs: 15-17 and 21-23 according to the disclosure.

FIG. 6 is a series of graphs demonstrating cytotoxicity against leukemia cells lines by BAFF-CAR-T cells.

DETAILED DESCRIPTION

Figure 3:
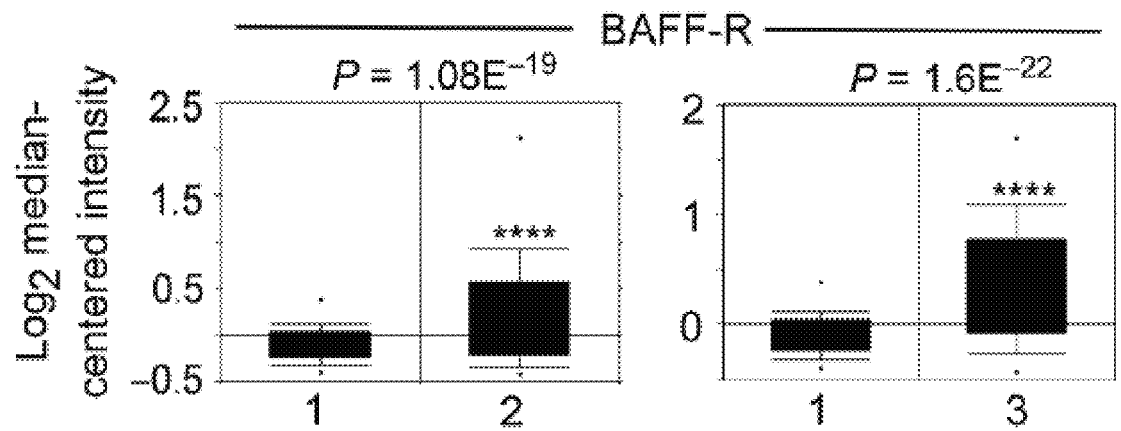
FIG. 3 includes graphs demonstrating increased expression of BAFF-R on the surface of ALL cells.

Example embodiments will now be described more fully hereinafter with reference to the accompanying figures in which example embodiments and representative data are shown. Whenever possible, the same reference numerals are used throughout the drawings to refer to the same or like parts. However, the embodiments may take on many different forms and should not be construed as limited to those specifically set forth herein. These example embodiments are provided so that this disclosure will be both thorough and complete, and will fully convey the scope of the claims to those skilled in the art.

Directional terms as used herein (e.g., up, down, right left, front, back, top, bottom) are made only with reference to the figures as drawn and are not intended to imply absolute orientation.

As used herein, the term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. When the term "about" is used in describing a value or an endpoint of a range, the disclosure should be understood to include the specific value or endpoint referred to. Whether or not a numerical value or endpoint of a range in the specification recites "about," the numerical value or endpoint of a range is intended to include two embodiments: one modified by "about," and one not modified by "about." It will be further understood that the endpoints of each of the ranges are significant both in relation to the other endpoint, and independently of the other endpoint.

The terms "substantial," "substantially," and variations thereof as used herein are intended to note that a described feature is equal or approximately equal to a value or description. For example, a "substantially planar" surface is intended to denote a surface that is planar or approximately planar. Moreover, "substantially" is intended to denote that two values are equal or approximately equal. In some embodiments, "substantially" may denote values within about 10% of each other, such as within about 5% of each other, or within about 2% of each other.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue. Thus, cells that are "free of" or "substantially free of T cell contamination" for example, are cells to which T cells are not actively added or batched into cell culture, but may be present in very small as a contaminant resulting from natural cell progression during expansion. Similarly, other components may be characterized as "free of" or "substantially free of" in the same manner.

Further, as used herein, the term "consisting essentially of" allows for elements not explicitly recited but excludes element that affect basic or novel characteristics of the inventions. As recited herein, the term "consisting of" excludes elements not expressly stated.

B-cell activating factor (BAFF) is a cytokine belonging to the tumor necrosis factor (TNF) ligand family. BAFF is abundantly produced by monocytes, macrophages, dendritic cells and stromal cells, which are main cellular components of MCL tumor microenvironment. BAFF signaling is essential for the generation of mature B cells and it helps survival of normal and malignant B cells. BAFF has at least three receptors: transmembrane activator and CAML interactor (TACI), B-cell maturation antigen (BCMA) and BAFF receptor (BAFF-R). Of these, BAFF-R is specific to BAFF while BCMA and TACI share another homologous ligand, APRIL. Signaling through BAFF-R mediates B cell survival. Virtually all mature B cell leukemias and lymphomas express BAFF receptor. Early B cells, which are counterparts of acute lymphocytic leukemia (ALL) do not express BAFF-R, but cells from patients with some cancers express high levels of BAFF-R, including ALL and mantle cell lymphoma (MCL) patients. Further, BAFF-R is expressed only on mature B cells, making it an attractive target for targeting and reducing side effects caused by off targeting. Thus, BAFF-R presents a target opportunity for treating such cancers, as well as autoimmune diseases where increased serum BAFF levels are often present.

In one example according to the present disclosure is a method of treating or preventing a disease or condition by targeting a receptor of BAFF. In another example according to the present disclosure is a method of treating or preventing a disease or condition by targeting a cell expressing or overexpressing a receptor of BAFF, such as BAFF-R. In an exemplary embodiment, the disease or condition is a cancer, such as a hematologic malignancy. In one embodiment, the hematologic malignancy can be any hematologic malignancy wherein the cancer cells express or overexpress a receptor of BAFF, including but not limited to acute lymphocytic leukemia, acute myeloid leukemia, chronic lymphocytic leukemia, chronic myeloid leukemia, hairy cell leukemia, diffuse large B-cell lymphoma, mantle cell lymphoma, follicular lymphoma, marginal zone lymphoma, Acute lymphoblastic leukemia, non-Hodgkin's lymphoma, Hodgkin's lymphoma, B cell malignancies, and multiple myeloma. In another exemplary embodiment, the disease or condition is an autoimmune disease, such as systemic lupus erythematosus, Sjogren's syndrome, narcolepsy, diabetes, pancreatitis, Crohn's disease, Celiac disease, ankylosing spondylitis, psoriasis, Grave's Disease, or rheumatoid arthritis. In another example the disease or condition is an abdominal aortic aneurysm with B cell involvement.

Conventional chimeric antigen receptor-T (CAR-T) cells use a single chain variable fragment of an antibody (Sc-Fv) to the corresponding tumor target antigen. Indeed, WO 2017/214167 reports a BAFF-R antibody that is capable of binding to human BAFF-R protein and induce antibody-dependent cellular cytotoxicity on BAFF-R expressing cells. These antibodies can form part of a chimeric antigen receptor (CAR) and are said to be used for the treatment of cancer. This antibody treatment approach, however, is limited to only those cells expressing BAFF-R. Because an antibody approach is specific for only one receptor, the prior art disclosure is limited in its approach. Provided herein is a BAFF-ligand-based CAR that can be used to target not only BAFF-R, but any receptor of BAFF, including, e.g., TACI and BCMA.

Instead of Sc-Fv, the present disclosure uses a ligand approach to hunt for receptors of BAFF, such as BAFF-R, TACI and BCMA, on the surface of, for example, tumor cells for CAR-T cell immunotherapy against a wide variety of cancers and autoimmune diseases. Using BAFF protein, BAFF-ligand-based CARs have been generated and are reported herein.

In the present disclosure, the "BAFF protein" or "BAFF" refers to any of the recombinant or naturally occurring forms of the B-cell activating factor as set forth in SEQ ID NO:1 or variants to homologs thereof that maintain BAFF activity (e.g. within at least about 80%, 85%, 90%, 95%, 96%, 97%, 98%, 99% or 100% activity compared to BAFF). Optionally, the variants or homologs thereof have at least 90%, 95%, 96%, 97%, 98%, 99% or 100% amino acid sequence identity (i.e. sequence homology) across the whole of SEQ ID NO:1 or a portion of SEQ ID NO:1.

As used herein, a "partial sequence" or "BAFF partial sequence" refers to a portion of SEQ ID NO:1 that maintains BAFF activity similar to that of the whole sequence, and in particular, an extracellular portion of BAFF that is responsible for binding with a receptor of BAFF. In one example of a partial sequence is a sequence comprising at least 95%, 90%, 85%, 80%, 75%, 70%, 65%, 60%, 55%, 50%, 45%, 40%, 35%, 30%, 25%, 20%, 15% or 10% of the naturally occurring BAFF sequence. Also contemplated are sequences having at least 90%, 95%, 96%, 97%, 98%, 99% or 100% amino acid sequence identity across the partial sequence. In one example, the partial BAFF sequence comprises amino acids 82-285 (SEQ ID NO:2) or a sequence having at least 90%, 95%, 96%, 97%, 98%, 99% or 100% amino acid sequence identity to SEQ ID NO:2. In another example, the BAFF partial sequence comprises amino acids 134-285 (SEQ ID NO:3) having at least 90%, 95%, 96%, 97%, 98%, 99% or 100% amino acid sequence identity to SEQ ID NO:3.

As used herein, "chimeric antigen receptor T cells" or "CAR-T" cells are T cells that have been genetically engineered to produce an artificial T cell receptor for use in immunotherapy. "Chimeric antigen receptor" or "CAR" are receptor proteins that have been engineered to give T cells the new ability to target a specific protein. CARs are recombinant receptors that provide both antigen-binding and T-cell activating functions. In an example according to the present disclosure, the CAR-T cells have been engineered to target a receptor of BAFF using BAFF as a ligand. CAR-T cell therapy is based on recognition of specific tumor antigen by genetically modified T cells, followed by intracellular signaling and activation of T cells, which subsequently leads to destruction of the tumor cell. In another example of the present disclosure, natural killer (NK) cells or natural killer T (NKT) cells are modified to express a CAR.

The present disclosure relates to CARs that have been engineered to express a BAFF ligand. FIG. 1 shows a schematic example of how a CAR according to the present disclosure can be designed. In one example, the CAR expresses the native human BAFF full sequence, i.e. SEQ ID NO:1. In other examples according to the present disclosure, the CAR expresses a partial sequence of BAFF. In one embodiment the partial sequence comprises an extracellular domain of BAFF. In another embodiment, the partial sequence comprises a domain involved in receptor binding, such as a BAFF-R, TACI or BCMA binding domain. In one embodiment, the partial sequence comprises amino acids 82-285 (SEQ ID NO:2) of BAFF. In another embodiment, the partial sequence comprises amino acids 134-285 (SEQ ID NO:3) of BAFF. In other examples, the BAFF sequence (full or partial) can be incorporated into the construct such that the BAFF domain is transposed so that the amino acid sequence is reversed. In other words, the amino acids that are at the C-terminal end in the native sequence become the amine terminus of the sequence, and the amino acids that are normally at the N-terminus become the C-terminal end of the sequence.

The CAR can further comprise one or more hinge domains. In one example, the hinge domain comprises a hinge domain of CD8a (SEQ ID NO:4), or a partial sequence thereof. In another example, the hinge domain comprises an amino acid sequence having at least 90%, 95%, 96%, 97%, 98%, 99% or 100% amino acid sequence identity to SEQ ID NO:4. In another example, the hinge domain comprises a hinge domain of IgG1 (SEQ ID NO:5), or a partial sequence thereof. In another example, the hinge domain comprises an amino acid sequence having at least 90%, 95%, 96%, 97%, 98%, 99% or 100% amino acid sequence identity to SEQ ID NO:5. In yet another example, the CAR cells of the present disclosure comprise a hinge domain of CD28. In yet another example, the CAR cells of the present disclosure comprise a hinge domain of FCγ/RIII.

The CAR further comprises one or more transmembrane domains. In one example, the CAR comprises a transmembrane domain of CD8α, such as that of SEQ ID NO:6. In another example, the transmembrane domain comprises an amino acid sequence having at least 90%, 95%, 96%, 97%, 98%, 99% or 100% amino acid sequence identity to SEQ ID NO:6. In another example, the CAR comprises a transmembrane domain of CD28, such as that of SEQ ID NO: 7. In another example, the transmembrane domain comprises an amino acid sequence having at least 90%, 95%, 96%, 97%, 98%, 99% or 100% amino acid sequence identity to SEQ ID NO:7. In one embodiment, the CAR comprises a hinge domain and a transmembrane domain.

The CAR can further comprise one or more intracellular domains. In one example, the CAR comprises an intracellular domain of 41BB, such as SEQ ID NO:8. In another example, the intracellular domain comprises an amino acid sequence having at least 90%, 95%, 96%, 97%, 98%, 99% or 100% amino acid sequence identity to SEQ ID NO:8. In another example, the CAR comprises an intracellular domain of CD28, such as that disclosed in SEQ ID NO:9. In another example, the intracellular domain comprises an amino acid sequence having at least 90%, 95%, 96%, 97%, 98%, 99% or 100% amino acid sequence identity to SEQ ID NO:9. In yet another embodiment, the CAR comprises an intracellular domain of CD3-zeta, such as that disclosed in SEQ ID NO:10. In another example, the intracellular domain comprises an amino acid sequence having at least 90%, 95%, 96%, 97%, 98%, 99% or 100% amino acid sequence identity to SEQ ID NO:10. In yet another example, the CAR comprises an intracellular domain of OX40 (SEQ ID NO:11). In another example, the intracellular domain comprises an amino acid sequence having at least 90%, 95%, 96%, 97%, 98%, 99% or 100% amino acid sequence identity to SEQ ID NO:11. According to the present disclosure, the CAR can comprise more than one intracellular domain. In one embodiment, the CAR comprises a hinge domain, a transmembrane domain, and one or more intracellular domain(s).

The CAR can further comprise a signaling peptide. In one example, the signaling peptide is a peptide according to SEQ ID NO:21 or a peptide having at least 90%, 95%, 96%, 97%, 98%, 99% or 100% amino acid sequence identity to SEQ ID NO:21. In another example, the signaling peptide is a peptide according to SEQ ID NO:22 or a peptide having at least 90%, 95%, 96%, 97%, 98%, 99% or 100% amino acid sequence identity to SEQ ID NO:22. In one embodiment, the CAR comprises a hinge domain, signaling domain, a transmembrane domain, and one or more intracellular domain(s).

Because distance between T cell and target cell is an important factor affecting tumor recognition and cytotoxicity, a linker domain can be incorporated between BAFF and the hinge domain or between the hinge domain and the transmembrane domain. In some embodiments, the linker comprises a simple alkyl chain, such as —$(CH_2)_n CH_3$ unit, wherein n is the number of $CH_2$ groups and can vary from 1-100, preferably 1-50, 1-20, or 1-10. In another example, the linker can be a peptide of 1-50 amino acids, such as 1-20 amino acids, or 1-10 amino acids. In a preferred embodiment, the linker comprises SEQ ID NO:12, or a variant thereof having at least 85% sequence homology to SEQ ID NO:12.

FIG. 2 shows a schematic of six exemplary CAR constructs according to the disclosure. The top schematic includes a BAFF full sequence, of which SEQ ID NO:15 is an example. The top middle schematic utilizes a BAFF partial sequence but is otherwise identical to the top schematic. SEQ ID NOs:16 & 17 are examples of such a construct. The middle bottom and bottom schematics employ the BAFF and partial BAFF sequences, respectively, but incorporate different hinge, transmembrane and intracellular regions. SEQ ID NO: 21 and SEQ ID NOs:22 & 23, respectively, are represented by these schematics.

The following examples are illustrative and are not intended to limit the scope of the invention as claimed.

EXAMPLES

Example 1

ALL Cells Express BAFF-R

To confirm BAFF-R expression in ALL cells, 359 pediatric and 147 adult ALL patient samples were compared with PBMCs from 74 healthy donors using the Haferlach Leukemia Oncomine database. In the present disclosure, the "peripheral blood mononuclear cells," "PBMCs" or "mononuclear cells" refer to mononuclear cells separated from peripheral blood typically used for anti-cancer immunotherapy. PBMCs may be obtained from a healthy person, a patient at risk of cancer, or a cancer patient. Collected blood samples (30 mL) from healthy donors were processed to isolate peripheral blood mononuclear cells (PBMCs) by density gradient separation using Ficoll-Paque. Samples were diluted with 1× volume of PBS (pH 7.2) and diluted blood (30 mL) was layered over 15 mL of Ficoll-Paque in a 50 mL conical tube. Samples were centrifuged (400×g, 30 min) at 20° C. in a swing-bucket rotor without brake. The resulting upper layer was aspirated, leaving the PBMC layer undisturbed. The PBMC layer was transferred to a new 50 mL conical tube, which was then filled with PBS and centrifuged (300×g, 10 min) at 20° C. The cell pellet was resuspended with PBS and centrifuged (300×g, 10 min) at 20° C. The cells were resuspended in 1× MojoSort buffer at density of 1×10$^8$/mL. The CD3+ T cells were then purified by MojoSort human CD3 T cell isolation kit (Biolegend).

As seen in FIG. 3, mRNA expression was significantly increased in both ALL patient samples. FIG. 3 show a significant increase in BAFF-R expression in pediatric (FIG. 3, 2) and adult (FIG. 3) as compared to healthy donors (1), showing that BAFF-R levels are increased in ALL cells as compared to healthy cells.

Figure 4:
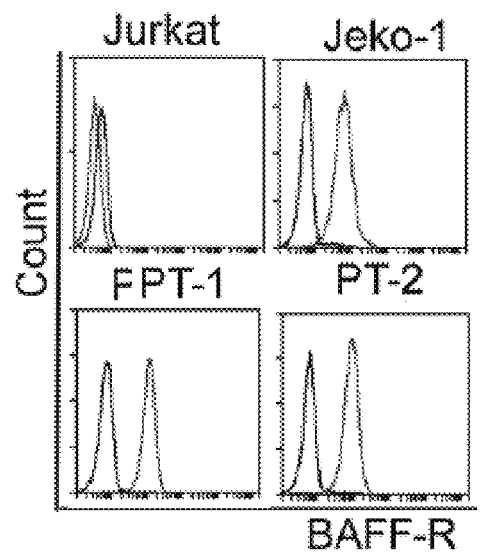
FIG. 4 shows flow cytometry histograms of BAFF-R expression in newly diagnosed and relapsed ALL patients.

BAFF-R expression was also measured in newly diagnosed ALL cells at the time of diagnosis. Using flow cytometry (see Vicioso, et al. "Combination Therapy for Treating Advanced Drug-Resistant Acute Lymphoblastic Leukemia" Cancer Immun. Res 7, 1106-1119 (2019), hereby incorporated by reference, for methods), levels of BAFF-R expression in newly diagnosed (FIG. 4 bottom left) and relapsed (FIG. 4, bottom right) ALL patients were measured and compared to Jurkat (negative control, top left) and Jeko-1 (positive control, top right) cells. In all graphs, the left histogram represents an unstained BAFF-R positive control; the right histogram represents cells stained with an anti-BAFF-R antibody.

Example 2

Development of BAFF-CAR-T Cells

The design of various BAFF-CAR-T cells was discussed above. Each construct was designed to include the BAFF protein (whole or partial sequence), a hinge domain, a transmembrane domain and one or more intracellular domains. The construct may also optionally include an extracellular signaling domain and a linker domain to optimize spacing. Each construct was cloned into a 3$^{rd}$ generation lentivirus vector and packaged in HEK293T cells.

Human PBMC cells were used to collect and purify CD3+ T cells as described above. The T cells were activated using Dynabeads human T-Activator CD3/CD28 (Gibco/Invitrogen). For activation of 1×10$^6$ of CD3+ T cells, mixing 25 μL Dynabeads with the T cells in 1.5 mL of complete culture medium (advanced RPMI medium 1640 with 2 mM L-glutamine, 10% FBS and 100 U/mL penicillin/streptomycin) in the presence of 50 U/mL of interleukin-2 (IL-2) (PeproTech). Cells were resuspended with beads in medium and distributes to one well of a 24-well plate. Cells were cultured in 5% $CO_2$ incubator at 37° C. for 24-48 hours to prepare for virus infection with concentrated lentivirus containing BAFF CAR.

Production of the lentivirus supernatants containing the BAFF-CAR was accomplished as follows. Lentiviral supernatant was produced using the packaging cell line, 293FT. Healthy 293FT cells were cultured in DMEM medium with 10% FBS with 100 U/mL penicillin/streptomycin. The day before vector transfection, 293FT cells were split to 5×10$^6$/10 cm tissue culture plate. Four plates of 293 FT cells were needed to make enough supernatants for concentration of lentivirus. For one 10 cm plate, 200 μL of Opti-MEM medium was added to an Eppendorf tube, followed by 3750 ng packaging plasmid psPax2, 1250 ng envelop plasmid pMD2G and 5000 ng of BAFF CAR vector. The tubes were mixed gently and then 10 μL of X-tremeGENE HP transfection reagent (Sigma catalog #06 366 236 001) was added, mixed gently and incubated for 20 minutes at RT. The DNA mixture was added dropwise into a 10 cm 293FT plate and incubated at 5% $CO_2$ incubator at 37° C. After an overnight culture, the medium was removed and replaced with 6 mL of fresh complete DMEM medium. Supernatants were collected at 48 h and 72 h after vector transfection from the four plates (23 mL in total) into 50 mL conical tube and centrifuge at 500×g for 10 min to remove cells debris. 23 mL of the clear supernatants was transferred to a new 50 mL conical tube, to which 7.6 mL of Lenti-X Concentrator (Clontech) was added, mixed and incubated at 4° C. overnight. The supernatants were centrifuged (1500×g, 45 min, 4° C.) and the supernatants removed to afford an off-white pellet. Pellets were resuspended in 1 mL complete advanced RMPI medium with IL-2 and prepared for virus transduction into CD3+ T cells.

Around 1×10$^6$ activated T cells together with Dynbeads were resuspended in 1 mL of complete advanced RPMI medium containing concentrated BAFF CAR and distributed in an amount of 100 μL into each well into total of 10-12 wells in round-bottom 96 well plate. T cells were spinoculated (3480 rpm, 22° C., 90 min). After centrifugation, cells were resuspended and collected with Dynabeads, then reseparated into 24-well plates again. 1 mL more complete advanced RPMI medium was added together with IL-2 50 U/mL, IL-7 10 ng/mL and IL-15 5 ng/mL. T cells were cultured in an incubator at 5% $CO_2$, 37° C. Fresh media with cytokines was added when the media in the culture became yellow. The Dynabeads was removed 4-5 days after initial T cells activation. The transduced T cells expanded exponentially 5-8 days after activation. T cell culture was maintained at density below 3×10$^6$ /mL and more complete media with cytokines was added as needed. BAFF CAR transduction efficiency in T cells was monitored 72 hours after virus transduction. Transduction was confirmed by either presence of GFP positive cells or BAFF staining using an anti-human BAFF antibody-APC conjugate (Biolegend). BAFF CAR T cells were used at day 7-10 for in vitro and in vivo experiments or frozen in 95% FBS+5% DMSO in liquid nitrogen for later use.

In one example, T cells were isolated from human blood, activated and transduced with SEQ ID NO:15 lentiviral particles. Transduction efficiency was estimated by GFP expression (data not shown). About 27% of CAR-T cells expressed the protein corresponding to SEQ ID NO:15.

Example 3

CAR-T Cells Kill Leukemia Cells In Vitro

The MCL cell line Jeko-1 and the ALL cell line RS4;11 were used as tumor targets to test the efficacy of the BAFF CAR-T cells. The cells were grown and transduced as described above using SEQ ID NO: 15 and SEQ ID NO:17. Tumor cell killing by BAFF CAR-T cells was analyzed using a calcein-AM assay purchased from Life Technologies. Target tumor cells (10×10$^6$) were labeled with (0.5 μmol/L) calcein-AM for 30 min at 37° C. Following staining, cells were washed with PBS, counted using Trypan blue (Sigma), and incubated with BAFF CAR-T cells for 4-6 hours at 5:1 or 10:1 ratio as indicated. The percentage of live tumor cells was analyzed by Annexin/PI negative and CD19 positive staining and the percentage lysis determined according to the following equation:

$$\% \text{ specific lysis} = 100 \times \frac{AFU \text{ mean experimental release} - AFU \text{ mean spontaneous release}}{AFU \text{ mean maximal release} - AFU \text{ mean spontaneous release}}$$

wherein "AFU mean spontaneous release" is calcein-AM release by target cells alone (in the absence of T cells);

"AFU mean maximal release" is calcein-AM release by target cells upon lysis by detergent; and "AFU mean experimental release" is calcein-AM release by target cells mixed with BAFF CAR-T cells.

Figure 5:
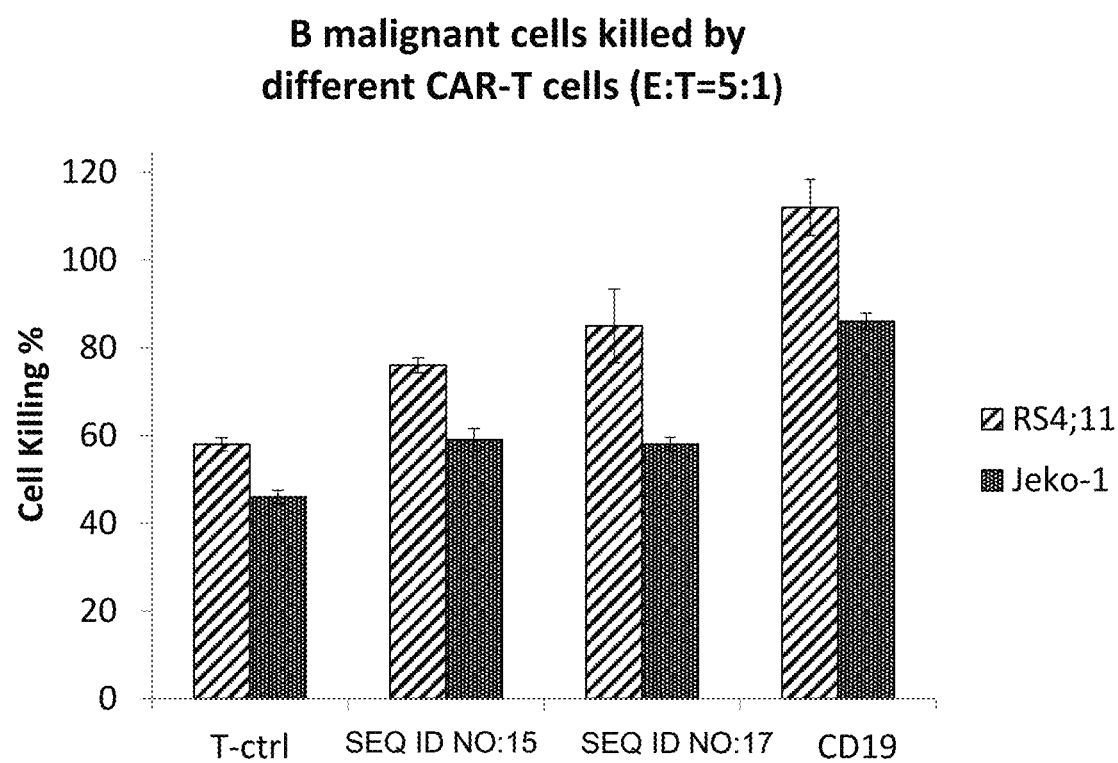
FIG. 5 demonstrates killing activity by a BAFF-CAR-T expressing SEQ ID NO:15 and SEQ ID NO:17 in MCL cells.

FIG. 5 shows the % cell killing (y-axis) for control T cells (left histogram), CAR-T cells expressing SEQ ID NO:15 (left middle), CAR-T cells expressing SEQ ID NO:17 (right middle), and anti CD19 CAR-T cells (right). For the MCL Jeko-1 cell line, cell killing following treatment with the control T cells resulted in about 45% MCL cell death and treatment with the CD19 CAR-T cells resulted in over 90% cell death. Treatment with the CAR-T cells expressing SEQ ID NO:15 and SEQ ID NO:17 resulted in approximately 60% cell death for both constructs. For the RS4;11 ALL cells, the CAR-T cells resulted in approximately 80% and 85% cell death. Treatment with the negative control demonstrated cell death of about 60% and treatment with the positive control resulted in nearly 100% cell death. These results demonstrate the viability of treatment of cancer cells with the CAR-T cells of the disclosure.

The cytotoxicity of RS4;11 cells was further studied following exposure to CAR-T cells expressing the construct of SEQ ID NO:15 and SEQ ID NO:22. FIG. 6 (top) shows the effect of treatment of RS4 cells with T cell control (left), CAR-T cells expressing SEQ ID NO:15 (middle) and CAR-T cells expressing SEQ ID NO:22 (right). Treatment with the negative control resulting in cell death of less than 10% of cells. Treatment with CAR-T cells expressing SEQ ID NO:15 and SEQ ID NO:22 resulted in cell killing of about 40% and 25%, respectively.

The cytotoxicity of Jeko-1 and RS4;11 cells were also studied following exposure to BAFF CAR-T cells expressing the construct expressing the partial BAFF sequence of SEQ ID NO:17. Following overnight incubation with control T cells (left), CAR-T cells (5:1 BAFF CAR-T:Jeko-1) (middle) and 10:1 (right), it was found that in all cases, the CAR-T cells more efficiently killed MCL and ALL cells compared to control. More specifically, at a 5:1 ratio of BAFF-CAR-T cells to tumor cells, Jeko-1 and RS4;11 cells had a cell death of about 40% and about 30%, respectively. Cell death was expectedly higher for 10:1 exposure, about 60% and about 40% for Jeko-1 and RS4;11 cells, respectively. Comparatively, the cell death for control T cells was less than 20% in both cases.

Example 5

Degranulation of CAR-T Cells

The degranulation of CAR-T cells following incubation with Jeko-1 cells was studied. Lysosomal-associated membrane protein-1 (LAMP-1 or CD107a) has been described as a marker of CD8+ T cell degranulation following stimulation. Cells were incubated with anti CD107 antibody and analyzed for CD107 positive staining using flow cytometry.

Figure 7:
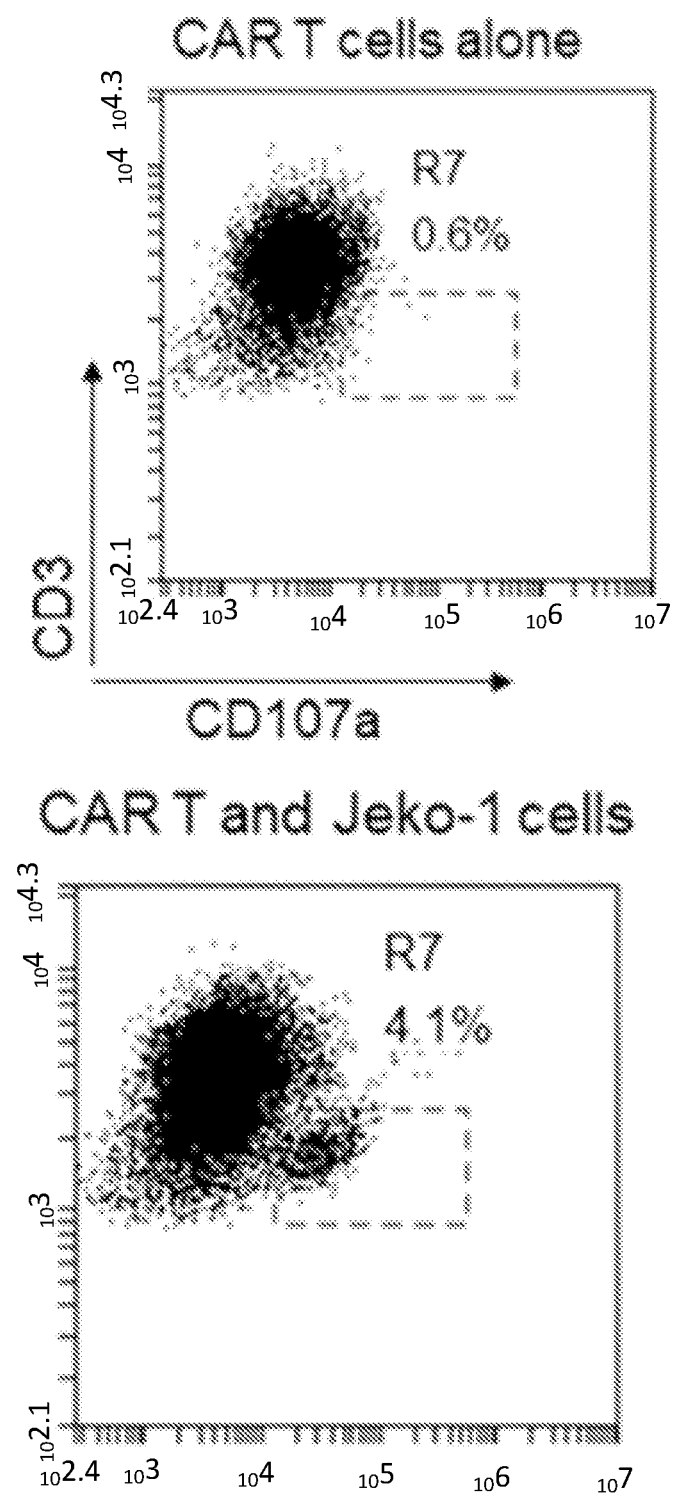
FIG. 7 is a scatter plot showing increased degranulation of CAR-T cells following incubation with Jeko-1 cells.

FIG. 7 shows the results of incubation of CAR-T cells alone (left) and CAR T and Jeko-1 cells (right). As can be seen, the percentage of CAR-T cells showing degranulation was about 6-fold higher when incubated with the cancer cells as compared to incubation alone. This suggests that CAR-T cells according to the present disclosure recognize and are activated in the presence of the MCL cells tested.

Example 6

Granzyme B Release Studies

Granzyme B is an important molecule that is responsible for T cell mediated cell death. It is a serine protease commonly found in the granules of natural killer cells (NK cells) and cytotoxic T cells. It is secreted by these cells along with the pore forming protein perforin to mediate apoptosis in target cells. Thus, release of granzyme B was measured following the incubation of cancer cells in the presence of BAFF-CAR-T cells. Supernatant was collected from CAR-T cell or CAR-T+target cell co-culture plates. Human GranzymeB Elisa kit (Biolegend) was used and experiments performed as specified by the manufacturer's instructions. Binding of GranzymeB was detected using a secondary antibody, streptavidin-HRP, and TMB substrate solution (provided with specified ELISA kit). Substrate conversion was stopped after 20 minutes with 100 µL stop solution (2 N $H_2SO_4$) (Biolegend). Plates were washed with PBS plus 0.05% Tween20 in between incubations. Assay diluent provided by the manufacturer or RPMI medium (Sigma) was used as negative controls, and specific standard proteins were used as positive controls. Standard reconstitutions and curves were generated as per manufacturer's instructions for each assay. Optical density values were obtained using a microplate reader set to 450 nm (Bio-Rad iMark Microplate reader). DETAILS.

Figure 8:
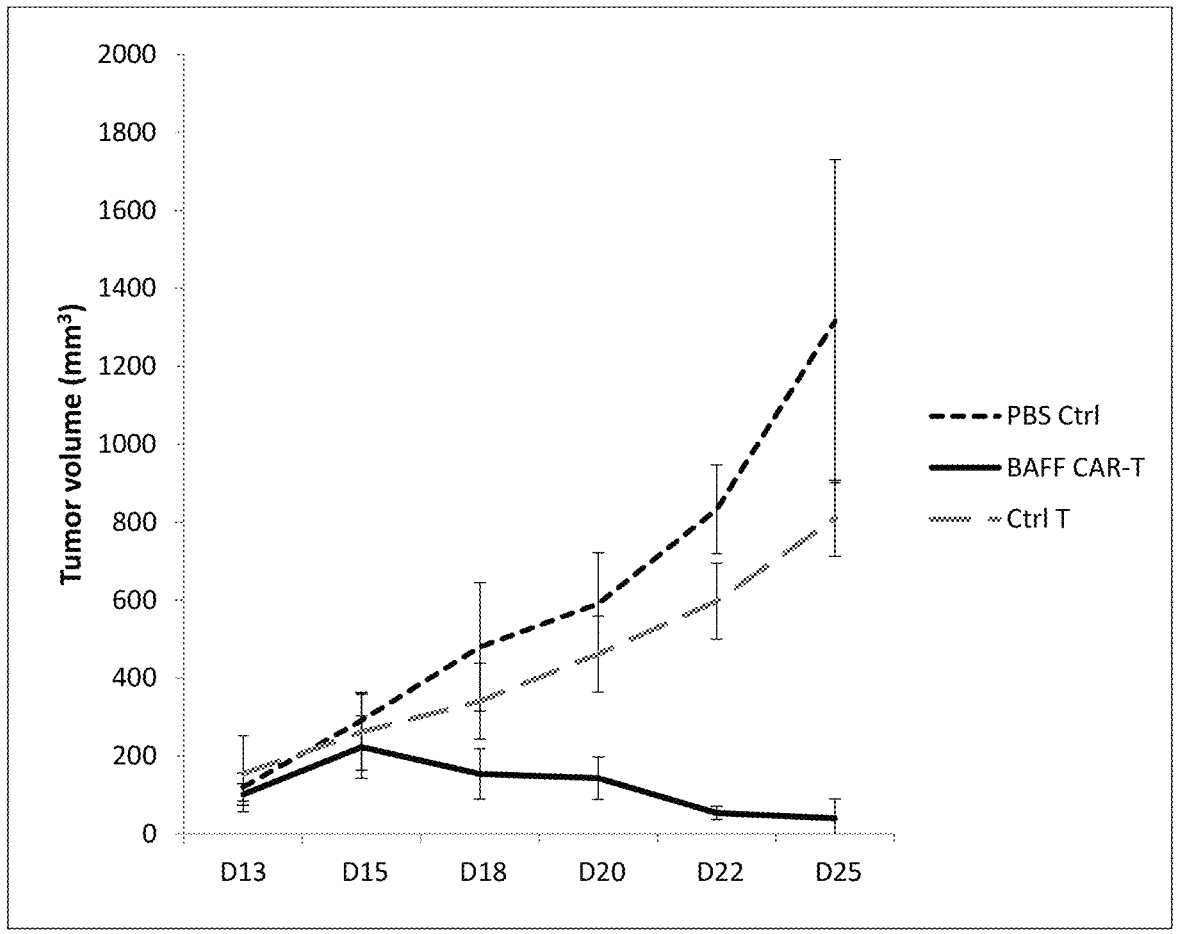
FIG. 8 is a graph showing tumor burden following treatment with BAFF-CAR-T cells.

FIG. 8 shows that granzyme B is released when the CAR-T cells according to the present disclosure are incubated with both RS4;11 or Jeko-1 cells. The cell ratio (5:1 or 10:1) did not appear to make a different in released granzyme levels, nor did cell type. In all cases, granzyme B was released at about the same amount. When CAR-T cells were incubated alone, no granzyme B excretion was detected (left). This suggests that the CAR-T cells according to the present disclosure recognize and are activated in the presence of the leukemic cells tested.

Example 7

BAFF-CAR T Cells Inhibit Tumor Growth In Vivo

BAFF-CAR T cells expressing SEQ ID NO:17 were tested in an in vivo study to determine whether the in vitro studies translate in vivo. Jeko-1 cells ($1 \times 10^6$ cells) were injected subcutaneously into immunocompromised mice. At day 14 following tumor cell implantation, the mice had palpable tumor. Mice were given an intratumor injection of either PBS solution (control), control T cells or BAFF-CAR-T cells. Tumor size was monitored on days 15, 18, 20, 22 and 25 post tumor cell injection.

Figure 9:
FIG. 9 shows photographs of mice implanted with a human leukemia cell line following treatment with PBS control (left) and BAFF-CAR-T cells (right) according to the present disclosure.
Figure 10:
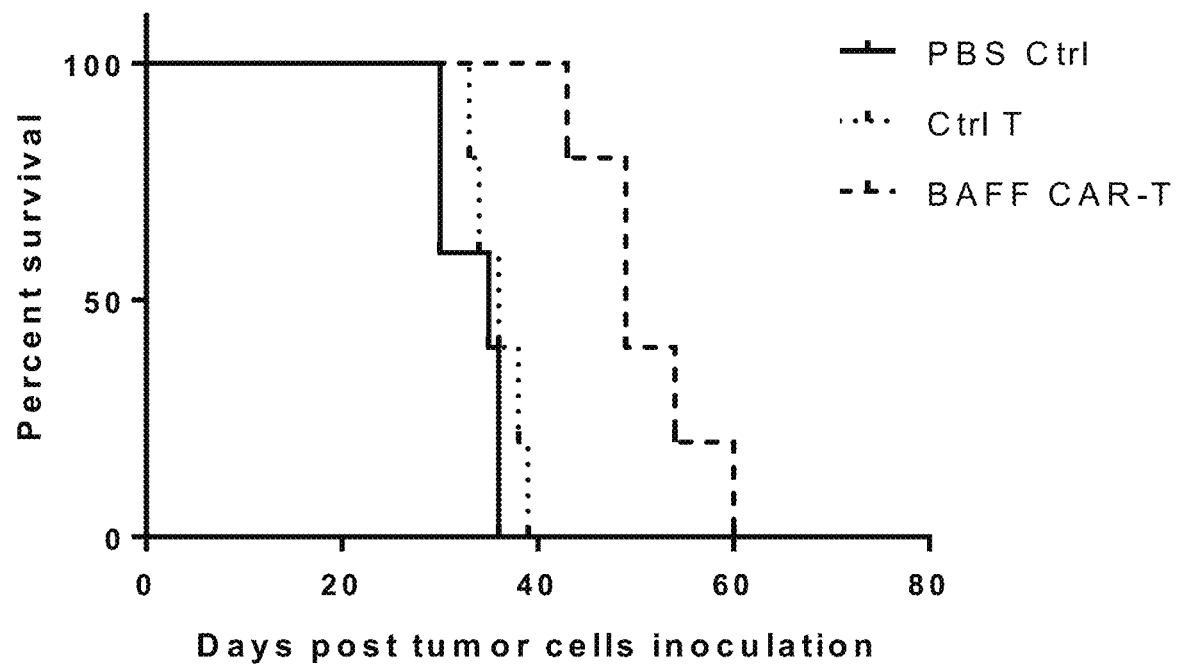
FIG. 10 is a line graph showing survival rates following treatment with control and BAFF-CAR-T cells according to the present disclosure.

FIG. 9 shows a plot of tumor volume ($mm^3$, y-axis) vs. day (x-axis). As can be seen, the tumors treated with PBS control and T cell control showed continued, uncontrolled tumor growth following treatment. The tumors treated with BAFF-CAR-T cells continued to grow for one day following treatment, at which time, tumor growth not only was stopped, but the tumors began to shrink. At day 25, 11 days following treatment, the tumors treated with BAFF-CAR-T cells were nearly entirely gone. FIG. 10 shows images of mice having Jeko-1 tumors treated with PBS (left) and BAFF-CAR-T cells (right).

Finally, survival of mice treated with BAFF-CAR-T cells was prolonged as compared to PBS and control T cells. The PBS treatment group exhibited 100% survival until about 35 days post tumor inoculation, and by 38 days post inoculation, all of the mice had died or been humanely euthanized due to tumor burden. Treatment with control T cells prolonged survival by about 2 days. The mice treated with BAFF-CAR-T cells experienced 100% survival until about 45 days, with all mice having died or been euthanized at day 60 post inoculation.

Many variations and modifications may be made to the above-described embodiments of the disclosure without departing substantially from the spirit and various principles of the disclosure. All such modifications and variations are intended to be included herein within the scope of this disclosure and protected by the following claims.

---

What is claimed is:

1. A chimeric receptor for targeting a receptor for B cell activating factor (BAFF) comprising an amino acid sequence with at least 95% sequence identity to SEQ ID NO: 20.

2. The chimeric receptor of claim 1, wherein the chimeric receptor comprises the amino acid sequence of SEQ ID NO: 20.

3. The chimeric receptor of claim 1, wherein the chimeric receptor consists essentially of the amino acid sequence of SEQ ID NO: 20.

4. An immune cell expressing the chimeric receptor of claim 1.

5. The immune cell of claim 4, wherein the immune cell is a human cell.

6. The immune cell of claim 4, wherein the immune cell is a T lymphocyte.

7. The immune cell of claim 4, wherein the immune cell is a cytotoxic T lymphocyte.

8. The immune cell of claim 4, wherein the immune cell is a natural killer T (NKT) cell.

9. The immune cell of claim 4, wherein the immune cell is a natural killer (NK) cell.

10. A vector comprising a nucleic acid that encodes the chimeric receptor of claim 1.

11. The chimeric receptor of claim 1, wherein the chimeric receptor consists essentially of an amino acid sequence with at least 95% sequence identity to SEQ ID NO: 20.

12. The chimeric receptor of claim 1, wherein the chimeric receptor consists of an amino acid sequence with at least 95% sequence identity to SEQ ID NO: 20.

13. The chimeric receptor of claim 1, wherein the chimeric receptor consists of the amino acid sequence of SEQ ID NO: 20.

* * * * *

SEQUENCE LISTING

<160> NUMBER OF SEQ ID NOS: 23

<210> SEQ ID NO 1
<211> LENGTH: 285
<212> TYPE: PRT
<213> ORGANISM: Homo sapiens

<400> SEQUENCE: 1

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
    130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
    210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
        275                 280                 285

<210> SEQ ID NO 2

```
<211> LENGTH: 204
<212> TYPE: PRT
<213> ORGANISM: Homo sapiens

<400> SEQUENCE: 2

Glu Leu Gln Gly His His Ala Glu Lys Leu Pro Ala Gly Ala Gly Ala
1               5                   10                  15

Pro Lys Ala Gly Leu Glu Glu Ala Pro Ala Val Thr Ala Gly Leu Lys
            20                  25                  30

Ile Phe Glu Pro Pro Ala Pro Gly Glu Gly Asn Ser Ser Gln Asn Ser
        35                  40                  45

Arg Asn Lys Arg Ala Val Gln Gly Pro Glu Gly Thr Val Thr Gln Asp
50                  55                  60

Cys Leu Gln Leu Ile Ala Asp Ser Glu Thr Pro Thr Ile Gln Lys Gly
65                  70                  75                  80

Ser Tyr Thr Phe Val Pro Trp Leu Leu Ser Phe Lys Arg Gly Ser Ala
                85                  90                  95

Leu Glu Glu Lys Glu Asn Lys Ile Leu Val Lys Glu Thr Gly Tyr Phe
            100                 105                 110

Phe Ile Tyr Gly Gln Val Leu Tyr Thr Asp Lys Thr Tyr Ala Met Gly
        115                 120                 125

His Leu Ile Gln Arg Lys Lys Val His Val Phe Gly Asp Glu Leu Ser
130                 135                 140

Leu Val Thr Leu Phe Arg Cys Ile Gln Asn Met Pro Glu Thr Leu Pro
145                 150                 155                 160

Asn Asn Ser Cys Tyr Ser Ala Gly Ile Ala Lys Leu Glu Glu Gly Asp
                165                 170                 175

Glu Leu Gln Leu Ala Ile Pro Arg Glu Asn Ala Gln Ile Ser Leu Asp
            180                 185                 190

Gly Asp Val Thr Phe Phe Gly Ala Leu Lys Leu Leu
        195                 200

<210> SEQ ID NO 3
<211> LENGTH: 152
<212> TYPE: PRT
<213> ORGANISM: Homo sapiens

<400> SEQUENCE: 3

Ala Val Gln Gly Pro Glu Glu Thr Val Thr Gln Asp Cys Leu Gln Leu
1               5                   10                  15

Ile Ala Asp Ser Glu Thr Pro Thr Ile Gln Lys Gly Ser Tyr Thr Phe
            20                  25                  30

Val Pro Trp Leu Leu Ser Phe Lys Arg Gly Ser Ala Leu Glu Glu Lys
        35                  40                  45

Glu Asn Lys Ile Leu Val Lys Glu Thr Gly Tyr Phe Phe Ile Tyr Gly
50                  55                  60

Gln Val Leu Tyr Thr Asp Lys Thr Tyr Ala Met Gly His Leu Ile Gln
65                  70                  75                  80

Arg Lys Lys Val His Val Phe Gly Asp Glu Leu Ser Leu Val Thr Leu
                85                  90                  95

Phe Arg Cys Ile Gln Asn Met Pro Glu Thr Leu Pro Asn Asn Ser Cys
            100                 105                 110

Tyr Ser Ala Gly Ile Ala Lys Leu Glu Glu Gly Asp Glu Leu Gln Leu
        115                 120                 125

Ala Ile Pro Arg Glu Asn Ala Gln Ile Ser Leu Asp Gly Asp Val Thr
130                 135                 140
```

```
Phe Phe Gly Ala Leu Lys Leu Leu
145                 150

<210> SEQ ID NO 4
<211> LENGTH: 45
<212> TYPE: PRT
<213> ORGANISM: Homo sapiens

<400> SEQUENCE: 4

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp
            35                  40                  45

<210> SEQ ID NO 5
<211> LENGTH: 20
<212> TYPE: PRT
<213> ORGANISM: Homo sapiens

<400> SEQUENCE: 5

Ala Glu Pro Lys Ser Pro Asp Lys Thr His Thr Cys Pro Pro Cys Pro
1               5                   10                  15

Lys Asp Pro Lys
            20

<210> SEQ ID NO 6
<211> LENGTH: 24
<212> TYPE: PRT
<213> ORGANISM: Homo sapiens

<400> SEQUENCE: 6

Ile Tyr Ile Trp Ala Pro Leu Ala Gly Thr Cys Gly Val Leu Leu Leu
1               5                   10                  15

Ser Leu Val Ile Thr Leu Tyr Cys
                20

<210> SEQ ID NO 7
<211> LENGTH: 27
<212> TYPE: PRT
<213> ORGANISM: Homo sapiens

<400> SEQUENCE: 7

Phe Trp Val Leu Val Val Val Gly Gly Val Leu Ala Cys Tyr Ser Leu
1               5                   10                  15

Leu Val Thr Val Ala Phe Ile Ile Phe Trp Val
                20                  25

<210> SEQ ID NO 8
<211> LENGTH: 42
<212> TYPE: PRT
<213> ORGANISM: Homo sapiens

<400> SEQUENCE: 8

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40
```

<210> SEQ ID NO 9
<211> LENGTH: 41
<212> TYPE: PRT
<213> ORGANISM: Homo sapiens

<400> SEQUENCE: 9

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
            35                  40

<210> SEQ ID NO 10
<211> LENGTH: 112
<212> TYPE: PRT
<213> ORGANISM: Homo sapiens

<400> SEQUENCE: 10

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 11
<211> LENGTH: 36
<212> TYPE: PRT
<213> ORGANISM: Homo sapiens

<400> SEQUENCE: 11

Arg Asp Gln Arg Leu Pro Pro Asp Ala His Lys Pro Pro Gly Gly Gly
1               5                   10                  15

Ser Phe Arg Thr Pro Ile Gln Glu Glu Gln Ala Asp Ala His Ser Thr
                20                  25                  30

Leu Ala Lys Ile
            35

<210> SEQ ID NO 12
<211> LENGTH: 7
<212> TYPE: PRT
<213> ORGANISM: Homo sapiens

<400> SEQUENCE: 12

Ser Gly Gly Gly Ser Asp Pro
1               5

<210> SEQ ID NO 13
<211> LENGTH: 20
<212> TYPE: PRT

<213> ORGANISM: Homo sapiens

<400> SEQUENCE: 13

Met Glu Thr Asp Thr Leu Leu Leu Trp Val Leu Leu Leu Trp Val Pro
1               5                   10                  15

Gly Ser Thr Gly
            20

<210> SEQ ID NO 14
<211> LENGTH: 21
<212> TYPE: PRT
<213> ORGANISM: Artificial Sequence
<220> FEATURE:
<223> OTHER INFORMATION: Synthetic Construct: CD8 alpha leader sequence

<400> SEQUENCE: 14

Met Ala Leu Pro Val Thr Ala Leu Leu Leu Pro Leu Ala Leu Leu Leu
1               5                   10                  15

His Ala Ala Arg Pro
            20

<210> SEQ ID NO 15
<211> LENGTH: 508
<212> TYPE: PRT
<213> ORGANISM: Artificial Sequence
<220> FEATURE:
<223> OTHER INFORMATION: Synthetic Construct: BAFF - CD8 hinge - CD8
      transmembrane - 41BB intracellular - CD3-zeta

<400> SEQUENCE: 15

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
    130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
    210                 215                 220

```
Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
            245                 250                 255

Asp Glu Leu Gln Leu Ala Ile Pro Arg Glu Asn Ala Gln Ile Ser Leu
        260                 265                 270

Asp Gly Asp Val Thr Phe Phe Gly Ala Leu Lys Leu Leu Thr Thr Thr
    275                 280                 285

Pro Ala Pro Arg Pro Pro Thr Pro Ala Pro Thr Ile Ala Ser Gln Pro
290                 295                 300

Leu Ser Leu Arg Pro Glu Ala Cys Arg Pro Ala Ala Gly Gly Ala Val
305                 310                 315                 320

His Thr Arg Gly Leu Asp Phe Ala Cys Asp Ile Tyr Ile Trp Ala Pro
                325                 330                 335

Leu Ala Gly Thr Cys Gly Val Leu Leu Leu Ser Leu Val Ile Thr Leu
            340                 345                 350

Tyr Cys Lys Arg Gly Arg Lys Lys Leu Leu Tyr Ile Phe Lys Gln Pro
        355                 360                 365

Phe Met Arg Pro Val Gln Thr Thr Gln Glu Glu Asp Gly Cys Ser Cys
370                 375                 380

Arg Phe Pro Glu Glu Glu Glu Gly Gly Cys Glu Leu Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
            420                 425                 430

Lys Arg Arg Gly Arg Asp Pro Glu Met Gly Gly Lys Pro Arg Arg Lys
        435                 440                 445

Asn Pro Gln Glu Gly Leu Tyr Asn Glu Leu Gln Lys Asp Lys Met Ala
    450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
            500                 505

<210> SEQ ID NO 16
<211> LENGTH: 427
<212> TYPE: PRT
<213> ORGANISM: Artificial Sequence
<220> FEATURE:
<223> OTHER INFORMATION: Synthetic Construct: BAFF partial - CD8 hinge -
      CD8 transmembrane - 41BB intracellular - CD3-zeta

<400> SEQUENCE: 16

Glu Leu Gln Gly His His Ala Glu Lys Leu Pro Ala Gly Ala Gly Ala
1               5                   10                  15

Pro Lys Ala Gly Leu Glu Glu Ala Pro Ala Val Thr Ala Gly Leu Lys
            20                  25                  30

Ile Phe Glu Pro Pro Ala Pro Gly Glu Gly Asn Ser Ser Gln Asn Ser
        35                  40                  45

Arg Asn Lys Arg Ala Val Gln Gly Pro Glu Glu Thr Val Thr Gln Asp
    50                  55                  60

Cys Leu Gln Leu Ile Ala Asp Ser Glu Thr Pro Thr Ile Gln Lys Gly
65                  70                  75                  80
```

```
Ser Tyr Thr Phe Val Pro Trp Leu Leu Ser Phe Lys Arg Gly Ser Ala
                85                  90                  95

Leu Glu Glu Lys Glu Asn Lys Ile Leu Val Lys Glu Thr Gly Tyr Phe
            100                 105                 110

Phe Ile Tyr Gly Gln Val Leu Tyr Thr Asp Lys Thr Tyr Ala Met Gly
        115                 120                 125

His Leu Ile Gln Arg Lys Lys Val His Val Phe Gly Asp Glu Leu Ser
130                 135                 140

Leu Val Thr Leu Phe Arg Cys Ile Gln Asn Met Pro Glu Thr Leu Pro
145                 150                 155                 160

Asn Asn Ser Cys Tyr Ser Ala Gly Ile Ala Lys Leu Glu Glu Gly Asp
                165                 170                 175

Glu Leu Gln Leu Ala Ile Pro Arg Glu Asn Ala Gln Ile Ser Leu Asp
            180                 185                 190

Gly Asp Val Thr Phe Phe Gly Ala Leu Lys Leu Leu Thr Thr Thr Pro
        195                 200                 205

Ala Pro Arg Pro Pro Thr Pro Ala Pro Thr Ile Ala Ser Gln Pro Leu
210                 215                 220

Ser Leu Arg Pro Glu Ala Cys Arg Pro Ala Ala Gly Gly Ala Val His
225                 230                 235                 240

Thr Arg Gly Leu Asp Phe Ala Cys Asp Ile Tyr Ile Trp Ala Pro Leu
                245                 250                 255

Ala Gly Thr Cys Gly Val Leu Leu Leu Ser Leu Val Ile Thr Leu Tyr
            260                 265                 270

Cys Lys Arg Gly Arg Lys Lys Leu Leu Tyr Ile Phe Lys Gln Pro Phe
        275                 280                 285

Met Arg Pro Val Gln Thr Thr Gln Glu Glu Asp Gly Cys Ser Cys Arg
290                 295                 300

Phe Pro Glu Glu Glu Glu Gly Gly Cys Glu Leu Arg Val Lys Phe Ser
305                 310                 315                 320

Arg Ser Ala Asp Ala Pro Ala Tyr Gln Gln Gly Gln Asn Gln Leu Tyr
                325                 330                 335

Asn Glu Leu Asn Leu Gly Arg Arg Glu Glu Tyr Asp Val Leu Asp Lys
            340                 345                 350

Arg Arg Gly Arg Asp Pro Glu Met Gly Gly Lys Pro Arg Arg Lys Asn
        355                 360                 365

Pro Gln Glu Gly Leu Tyr Asn Glu Leu Gln Lys Asp Lys Met Ala Glu
370                 375                 380

Ala Tyr Ser Glu Ile Gly Met Lys Gly Glu Arg Arg Arg Gly Lys Gly
385                 390                 395                 400

His Asp Gly Leu Tyr Gln Gly Leu Ser Thr Ala Thr Lys Asp Thr Tyr
                405                 410                 415

Asp Ala Leu His Met Gln Ala Leu Pro Pro Arg
            420                 425

<210> SEQ ID NO 17
<211> LENGTH: 375
<212> TYPE: PRT
<213> ORGANISM: Artificial Sequence
<220> FEATURE:
<223> OTHER INFORMATION: Synthetic Construct: BAFF partial - CD8 hinge -
      CD8 transmembrane - 41BB intracellular - CD3-zeta

<400> SEQUENCE: 17

Ala Val Gln Gly Pro Glu Glu Thr Val Thr Gln Asp Cys Leu Gln Leu
```

```
1               5                   10                  15

Ile Ala Asp Ser Glu Thr Pro Thr Ile Gln Lys Gly Ser Tyr Thr Phe
            20                  25                  30

Val Pro Trp Leu Leu Ser Phe Lys Arg Gly Ser Ala Leu Glu Glu Lys
            35                  40                  45

Glu Asn Lys Ile Leu Val Lys Glu Thr Gly Tyr Phe Phe Ile Tyr Gly
    50                  55                  60

Gln Val Leu Tyr Thr Asp Lys Thr Tyr Ala Met Gly His Leu Ile Gln
65                  70                  75                  80

Arg Lys Lys Val His Val Phe Gly Asp Glu Leu Ser Leu Val Thr Leu
                85                  90                  95

Phe Arg Cys Ile Gln Asn Met Pro Glu Thr Leu Pro Asn Asn Ser Cys
            100                 105                 110

Tyr Ser Ala Gly Ile Ala Lys Leu Glu Glu Gly Asp Glu Leu Gln Leu
            115                 120                 125

Ala Ile Pro Arg Glu Asn Ala Gln Ile Ser Leu Asp Gly Asp Val Thr
130                 135                 140

Phe Phe Gly Ala Leu Lys Leu Leu Thr Thr Thr Pro Ala Pro Arg Pro
145                 150                 155                 160

Pro Thr Pro Ala Pro Thr Ile Ala Ser Gln Pro Leu Ser Leu Arg Pro
            165                 170                 175

Glu Ala Cys Arg Pro Ala Ala Gly Gly Ala Val His Thr Arg Gly Leu
            180                 185                 190

Asp Phe Ala Cys Asp Ile Tyr Ile Trp Ala Pro Leu Ala Gly Thr Cys
            195                 200                 205

Gly Val Leu Leu Leu Ser Leu Val Ile Thr Leu Tyr Cys Lys Arg Gly
            210                 215                 220

Arg Lys Lys Leu Leu Tyr Ile Phe Lys Gln Pro Phe Met Arg Pro Val
225                 230                 235                 240

Gln Thr Thr Gln Glu Glu Asp Gly Cys Ser Cys Arg Phe Pro Glu Glu
            245                 250                 255

Glu Glu Gly Gly Cys Glu Leu Arg Val Lys Phe Ser Arg Ser Ala Asp
            260                 265                 270

Ala Pro Ala Tyr Gln Gln Gly Gln Asn Gln Leu Tyr Asn Glu Leu Asn
            275                 280                 285

Leu Gly Arg Arg Glu Glu Tyr Asp Val Leu Asp Lys Arg Arg Gly Arg
            290                 295                 300

Asp Pro Glu Met Gly Gly Lys Pro Arg Arg Lys Asn Pro Gln Glu Gly
305                 310                 315                 320

Leu Tyr Asn Glu Leu Gln Lys Asp Lys Met Ala Glu Ala Tyr Ser Glu
            325                 330                 335

Ile Gly Met Lys Gly Glu Arg Arg Arg Gly Lys Gly His Asp Gly Leu
            340                 345                 350

Tyr Gln Gly Leu Ser Thr Ala Thr Lys Asp Thr Tyr Asp Ala Leu His
            355                 360                 365

Met Gln Ala Leu Pro Pro Arg
            370                 375

<210> SEQ ID NO 18
<211> LENGTH: 528
<212> TYPE: PRT
<213> ORGANISM: Artificial Sequence
<220> FEATURE:
<223> OTHER INFORMATION: Synthetic Construct: BAFF - IgG1 hinge - CD28
      transmb - CD28 and OX signalling - CD3 zeta signalling
```

<400> SEQUENCE: 18

| | | | | | | | | | | | | | | |
|---|---|---|---|---|---|---|---|---|---|---|---|---|---|---|
| Met | Asp | Asp | Ser | Thr | Glu | Arg | Glu | Gln | Ser | Arg | Leu | Thr | Ser | Cys | Leu |
| 1 | | | | 5 | | | | | 10 | | | | | 15 | |
| Lys | Lys | Arg | Glu | Glu | Met | Lys | Leu | Lys | Glu | Cys | Val | Ser | Ile | Leu | Pro |
| | | | 20 | | | | | 25 | | | | | 30 | | |
| Arg | Lys | Glu | Ser | Pro | Ser | Val | Arg | Ser | Ser | Lys | Asp | Gly | Lys | Leu | Leu |
| | | 35 | | | | | 40 | | | | | 45 | | | |
| Ala | Ala | Thr | Leu | Leu | Ala | Leu | Leu | Ser | Cys | Cys | Leu | Thr | Val | Val |
| | 50 | | | | | 55 | | | | | 60 | | | | |
| Ser | Phe | Tyr | Gln | Val | Ala | Ala | Leu | Gln | Gly | Asp | Leu | Ala | Ser | Leu | Arg |
| 65 | | | | | 70 | | | | | 75 | | | | | 80 |
| Ala | Glu | Leu | Gln | Gly | His | His | Ala | Glu | Lys | Leu | Pro | Ala | Gly | Ala | Gly |
| | | | | 85 | | | | | 90 | | | | | 95 | |
| Ala | Pro | Lys | Ala | Gly | Leu | Glu | Glu | Ala | Pro | Ala | Val | Thr | Ala | Gly | Leu |
| | | | 100 | | | | | 105 | | | | | 110 | | |
| Lys | Ile | Phe | Glu | Pro | Pro | Ala | Pro | Gly | Glu | Gly | Asn | Ser | Ser | Gln | Asn |
| | | 115 | | | | | 120 | | | | | 125 | | | |
| Ser | Arg | Asn | Lys | Arg | Ala | Val | Gln | Gly | Pro | Glu | Glu | Thr | Val | Thr | Gln |
| | 130 | | | | | 135 | | | | | 140 | | | | |
| Asp | Cys | Leu | Gln | Leu | Ile | Ala | Asp | Ser | Glu | Thr | Pro | Thr | Ile | Gln | Lys |
| 145 | | | | | 150 | | | | | 155 | | | | | 160 |
| Gly | Ser | Tyr | Thr | Phe | Val | Pro | Trp | Leu | Leu | Ser | Phe | Lys | Arg | Gly | Ser |
| | | | | 165 | | | | | 170 | | | | | 175 | |
| Ala | Leu | Glu | Glu | Lys | Glu | Asn | Lys | Ile | Leu | Val | Lys | Glu | Thr | Gly | Tyr |
| | | | 180 | | | | | 185 | | | | | 190 | | |
| Phe | Phe | Ile | Tyr | Gly | Gln | Val | Leu | Tyr | Thr | Asp | Lys | Thr | Tyr | Ala | Met |
| | | 195 | | | | | 200 | | | | | 205 | | | |
| Gly | His | Leu | Ile | Gln | Arg | Lys | Lys | Val | His | Val | Phe | Gly | Asp | Glu | Leu |
| | 210 | | | | | 215 | | | | | 220 | | | | |
| Ser | Leu | Val | Thr | Leu | Phe | Arg | Cys | Ile | Gln | Asn | Met | Pro | Glu | Thr | Leu |
| 225 | | | | | 230 | | | | | 235 | | | | | 240 |
| Pro | Asn | Asn | Ser | Cys | Tyr | Ser | Ala | Gly | Ile | Ala | Lys | Leu | Glu | Glu | Gly |
| | | | | 245 | | | | | 250 | | | | | 255 | |
| Asp | Glu | Leu | Gln | Leu | Ala | Ile | Pro | Arg | Glu | Asn | Ala | Gln | Ile | Ser | Leu |
| | | | 260 | | | | | 265 | | | | | 270 | | |
| Asp | Gly | Asp | Val | Thr | Phe | Phe | Gly | Ala | Leu | Lys | Leu | Leu | Ser | Gly | Gly |
| | | 275 | | | | | 280 | | | | | 285 | | | |
| Gly | Ser | Asp | Pro | Ala | Glu | Pro | Lys | Ser | Pro | Asp | Lys | Thr | His | Thr | Cys |
| | 290 | | | | | 295 | | | | | 300 | | | | |
| Pro | Pro | Cys | Pro | Lys | Asp | Pro | Lys | Phe | Trp | Val | Leu | Val | Val | Val | Gly |
| 305 | | | | | 310 | | | | | 315 | | | | | 320 |
| Gly | Val | Leu | Ala | Cys | Tyr | Ser | Leu | Leu | Val | Thr | Val | Ala | Phe | Ile | Ile |
| | | | | 325 | | | | | 330 | | | | | 335 | |
| Phe | Trp | Val | Arg | Ser | Lys | Arg | Ser | Arg | Leu | Leu | His | Ser | Asp | Tyr | Met |
| | | | 340 | | | | | 345 | | | | | 350 | | |
| Asn | Met | Thr | Pro | Arg | Arg | Pro | Gly | Pro | Thr | Arg | Lys | His | Tyr | Gln | Pro |
| | | 355 | | | | | 360 | | | | | 365 | | | |
| Tyr | Ala | Pro | Pro | Arg | Asp | Phe | Ala | Ala | Tyr | Arg | Ser | Arg | Asp | Gln | Arg |
| | 370 | | | | | 375 | | | | | 380 | | | | |
| Leu | Pro | Pro | Asp | Ala | His | Lys | Pro | Pro | Gly | Gly | Gly | Ser | Phe | Arg | Thr |
| 385 | | | | | 390 | | | | | 395 | | | | | 400 |
| Pro | Ile | Gln | Glu | Glu | Gln | Ala | Asp | Ala | His | Ser | Thr | Leu | Ala | Lys | Ile |

Arg Val Lys Phe Ser Arg Ser Ala Asp Ala Pro Ala Tyr Gln Gln Gly
                420                 425                 430

Gln Asn Gln Leu Tyr Asn Glu Leu Asn Leu Gly Arg Arg Glu Glu Tyr
            435                 440                 445

Asp Val Leu Asp Lys Arg Arg Gly Arg Asp Pro Glu Met Gly Gly Lys
        450                 455                 460

Pro Arg Arg Lys Asn Pro Gln Glu Gly Leu Tyr Asn Glu Leu Gln Lys
465                 470                 475                 480

Asp Lys Met Ala Glu Ala Tyr Ser Glu Ile Gly Met Lys Gly Glu Arg
                485                 490                 495

Arg Arg Gly Lys Gly His Asp Gly Leu Tyr Gln Gly Leu Ser Thr Ala
            500                 505                 510

Thr Lys Asp Thr Tyr Asp Ala Leu His Met Gln Ala Leu Pro Pro Arg
        515                 520                 525

<210> SEQ ID NO 19
<211> LENGTH: 447
<212> TYPE: PRT
<213> ORGANISM: Artificial Sequence
<220> FEATURE:
<223> OTHER INFORMATION: Synthetic Construct: BAFF parital - IgG1
      hinge - CD28 transmb - CD28 and OX signalling - CD3 zeta
      signalling

<400> SEQUENCE: 19

Glu Leu Gln Gly His His Ala Glu Lys Leu Pro Ala Gly Ala Gly Ala
1               5                   10                  15

Pro Lys Ala Gly Leu Glu Glu Ala Pro Ala Val Thr Ala Gly Leu Lys
                20                  25                  30

Ile Phe Glu Pro Pro Ala Pro Gly Glu Gly Asn Ser Ser Gln Asn Ser
            35                  40                  45

Arg Asn Lys Arg Ala Val Gln Gly Pro Glu Glu Thr Val Thr Gln Asp
        50                  55                  60

Cys Leu Gln Leu Ile Ala Asp Ser Glu Thr Pro Thr Ile Gln Lys Gly
65                  70                  75                  80

Ser Tyr Thr Phe Val Pro Trp Leu Leu Ser Phe Lys Arg Gly Ser Ala
                85                  90                  95

Leu Glu Glu Lys Glu Asn Lys Ile Leu Val Lys Glu Thr Gly Tyr Phe
            100                 105                 110

Phe Ile Tyr Gly Gln Val Leu Tyr Thr Asp Lys Thr Tyr Ala Met Gly
        115                 120                 125

His Leu Ile Gln Arg Lys Lys Val His Val Phe Gly Asp Glu Leu Ser
130                 135                 140

Leu Val Thr Leu Phe Arg Cys Ile Gln Asn Met Pro Glu Thr Leu Pro
145                 150                 155                 160

Asn Asn Ser Cys Tyr Ser Ala Gly Ile Ala Lys Leu Glu Glu Gly Asp
                165                 170                 175

Glu Leu Gln Leu Ala Ile Pro Arg Glu Asn Ala Gln Ile Ser Leu Asp
            180                 185                 190

Gly Asp Val Thr Phe Phe Gly Ala Leu Lys Leu Leu Ser Gly Gly Gly
        195                 200                 205

Ser Asp Pro Ala Glu Pro Lys Ser Pro Asp Lys Thr His Thr Cys Pro
210                 215                 220

Pro Cys Pro Lys Asp Pro Lys Phe Trp Val Leu Val Val Val Gly Gly
225                 230                 235                 240

```
Val Leu Ala Cys Tyr Ser Leu Leu Val Thr Val Ala Phe Ile Ile Phe
                245                 250                 255

Trp Val Arg Ser Lys Arg Ser Arg Leu Leu His Ser Asp Tyr Met Asn
            260                 265                 270

Met Thr Pro Arg Arg Pro Gly Pro Thr Arg Lys His Tyr Gln Pro Tyr
            275                 280                 285

Ala Pro Pro Arg Asp Phe Ala Ala Tyr Arg Ser Arg Asp Gln Arg Leu
        290                 295                 300

Pro Pro Asp Ala His Lys Pro Pro Gly Gly Gly Ser Phe Arg Thr Pro
305                 310                 315                 320

Ile Gln Glu Glu Gln Ala Asp Ala His Ser Thr Leu Ala Lys Ile Arg
                325                 330                 335

Val Lys Phe Ser Arg Ser Ala Asp Ala Pro Ala Tyr Gln Gln Gly Gln
            340                 345                 350

Asn Gln Leu Tyr Asn Glu Leu Asn Leu Gly Arg Arg Glu Glu Tyr Asp
        355                 360                 365

Val Leu Asp Lys Arg Arg Gly Arg Asp Pro Glu Met Gly Gly Lys Pro
    370                 375                 380

Arg Arg Lys Asn Pro Gln Glu Gly Leu Tyr Asn Glu Leu Gln Lys Asp
385                 390                 395                 400

Lys Met Ala Glu Ala Tyr Ser Glu Ile Gly Met Lys Gly Glu Arg Arg
                405                 410                 415

Arg Gly Lys Gly His Asp Gly Leu Tyr Gln Gly Leu Ser Thr Ala Thr
            420                 425                 430

Lys Asp Thr Tyr Asp Ala Leu His Met Gln Ala Leu Pro Pro Arg
        435                 440                 445

<210> SEQ ID NO 20
<211> LENGTH: 395
<212> TYPE: PRT
<213> ORGANISM: Artificial Sequence
<220> FEATURE:
<223> OTHER INFORMATION: Synthetic Construct: BAFF parital - IgG1
      hinge - CD28 transmb - CD28 and OX signalling - CD3 zeta
      signalling

<400> SEQUENCE: 20

Ala Val Gln Gly Pro Glu Glu Thr Val Thr Gln Asp Cys Leu Gln Leu
1               5                   10                  15

Ile Ala Asp Ser Glu Thr Pro Thr Ile Gln Lys Gly Ser Tyr Thr Phe
            20                  25                  30

Val Pro Trp Leu Leu Ser Phe Lys Arg Gly Ser Ala Leu Glu Glu Lys
        35                  40                  45

Glu Asn Lys Ile Leu Val Lys Glu Thr Gly Tyr Phe Phe Ile Tyr Gly
50                  55                  60

Gln Val Leu Tyr Thr Asp Lys Thr Tyr Ala Met Gly His Leu Ile Gln
65                  70                  75                  80

Arg Lys Lys Val His Val Phe Gly Asp Glu Leu Ser Leu Val Thr Leu
                85                  90                  95

Phe Arg Cys Ile Gln Asn Met Pro Glu Thr Leu Pro Asn Asn Ser Cys
            100                 105                 110

Tyr Ser Ala Gly Ile Ala Lys Leu Glu Glu Gly Asp Glu Leu Gln Leu
        115                 120                 125

Ala Ile Pro Arg Glu Asn Ala Gln Ile Ser Leu Asp Gly Asp Val Thr
130                 135                 140
```

```
Phe Phe Gly Ala Leu Lys Leu Leu Ser Gly Gly Ser Asp Pro Ala
145                 150                 155                 160

Glu Pro Lys Ser Pro Asp Lys Thr His Thr Cys Pro Pro Cys Pro Lys
            165                 170                 175

Asp Pro Lys Phe Trp Val Leu Val Val Val Gly Gly Val Leu Ala Cys
            180                 185                 190

Tyr Ser Leu Leu Val Thr Val Ala Phe Ile Ile Phe Trp Val Arg Ser
            195                 200                 205

Lys Arg Ser Arg Leu Leu His Ser Asp Tyr Met Asn Met Thr Pro Arg
210                 215                 220

Arg Pro Gly Pro Thr Arg Lys His Tyr Gln Pro Tyr Ala Pro Pro Arg
225                 230                 235                 240

Asp Phe Ala Ala Tyr Arg Ser Arg Asp Gln Arg Leu Pro Pro Asp Ala
                245                 250                 255

His Lys Pro Pro Gly Gly Ser Phe Arg Thr Pro Ile Gln Glu Glu
                260                 265                 270

Gln Ala Asp Ala His Ser Thr Leu Ala Lys Ile Arg Val Lys Phe Ser
            275                 280                 285

Arg Ser Ala Asp Ala Pro Ala Tyr Gln Gln Gly Gln Asn Gln Leu Tyr
290                 295                 300

Asn Glu Leu Asn Leu Gly Arg Arg Glu Glu Tyr Asp Val Leu Asp Lys
305                 310                 315                 320

Arg Arg Gly Arg Asp Pro Glu Met Gly Gly Lys Pro Arg Arg Lys Asn
                325                 330                 335

Pro Gln Glu Gly Leu Tyr Asn Glu Leu Gln Lys Asp Lys Met Ala Glu
            340                 345                 350

Ala Tyr Ser Glu Ile Gly Met Lys Gly Glu Arg Arg Arg Gly Lys Gly
            355                 360                 365

His Asp Gly Leu Tyr Gln Gly Leu Ser Thr Ala Thr Lys Asp Thr Tyr
370                 375                 380

Asp Ala Leu His Met Gln Ala Leu Pro Pro Arg
385                 390                 395

<210> SEQ ID NO 21
<211> LENGTH: 547
<212> TYPE: PRT
<213> ORGANISM: Artificial Sequence
<220> FEATURE:
<223> OTHER INFORMATION: Synthetic Construct: Signal peptide - BAFF -
      linker - IgG1 hinge - CD28 transmb - CD28 and OX40 signalling -
      CD3 zeta signalling

<400> SEQUENCE: 21

Met Glu Thr Asp Thr Leu Leu Leu Trp Val Leu Leu Leu Trp Val Pro
1               5                   10                  15

Gly Ser Thr Gly Asp Asp Ser Thr Glu Arg Glu Gln Ser Arg Leu Thr
            20                  25                  30

Ser Cys Leu Lys Lys Arg Glu Glu Met Lys Leu Lys Glu Cys Val Ser
        35                  40                  45

Ile Leu Pro Arg Lys Glu Ser Pro Ser Val Arg Ser Ser Lys Asp Gly
    50                  55                  60

Lys Leu Leu Ala Ala Thr Leu Leu Leu Ala Leu Leu Ser Cys Cys Leu
65                  70                  75                  80

Thr Val Val Ser Phe Tyr Gln Val Ala Ala Leu Gln Gly Asp Leu Ala
                85                  90                  95

Ser Leu Arg Ala Glu Leu Gln Gly His His Ala Glu Lys Leu Pro Ala
```

-continued

```
                100                 105                 110
Gly Ala Gly Ala Pro Lys Ala Gly Leu Glu Glu Ala Pro Ala Val Thr
            115                 120                 125

Ala Gly Leu Lys Ile Phe Glu Pro Ala Pro Gly Glu Gly Asn Ser
        130                 135                 140

Ser Gln Asn Ser Arg Asn Lys Arg Ala Val Gln Gly Pro Glu Glu Thr
145                 150                 155                 160

Val Thr Gln Asp Cys Leu Gln Leu Ile Ala Asp Ser Glu Thr Pro Thr
                165                 170                 175

Ile Gln Lys Gly Ser Tyr Thr Phe Val Pro Trp Leu Leu Ser Phe Lys
            180                 185                 190

Arg Gly Ser Ala Leu Glu Glu Lys Glu Asn Lys Ile Leu Val Lys Glu
        195                 200                 205

Thr Gly Tyr Phe Phe Ile Tyr Gly Gln Val Leu Tyr Thr Asp Lys Thr
    210                 215                 220

Tyr Ala Met Gly His Leu Ile Gln Arg Lys Lys Val His Val Phe Gly
225                 230                 235                 240

Asp Glu Leu Ser Leu Val Thr Leu Phe Arg Cys Ile Gln Asn Met Pro
                245                 250                 255

Glu Thr Leu Pro Asn Asn Ser Cys Tyr Ser Ala Gly Ile Ala Lys Leu
            260                 265                 270

Glu Glu Gly Asp Glu Leu Gln Leu Ala Ile Pro Arg Glu Asn Ala Gln
        275                 280                 285

Ile Ser Leu Asp Gly Asp Val Thr Phe Phe Gly Ala Leu Lys Leu Leu
    290                 295                 300

Ser Gly Gly Gly Ser Asp Pro Ala Glu Pro Lys Ser Pro Asp Lys Thr
305                 310                 315                 320

His Thr Cys Pro Pro Cys Pro Lys Asp Pro Lys Phe Trp Val Leu Val
                325                 330                 335

Val Val Gly Gly Val Leu Ala Cys Tyr Ser Leu Leu Val Thr Val Ala
            340                 345                 350

Phe Ile Ile Phe Trp Val Arg Ser Lys Arg Ser Arg Leu Leu His Ser
        355                 360                 365

Asp Tyr Met Asn Met Thr Pro Arg Arg Pro Gly Pro Thr Arg Lys His
    370                 375                 380

Tyr Gln Pro Tyr Ala Pro Pro Arg Asp Phe Ala Ala Tyr Arg Ser Arg
385                 390                 395                 400

Asp Gln Arg Leu Pro Pro Asp Ala His Lys Pro Pro Gly Gly Gly Ser
                405                 410                 415

Phe Arg Thr Pro Ile Gln Glu Glu Gln Ala Asp Ala His Ser Thr Leu
            420                 425                 430

Ala Lys Ile Arg Val Lys Phe Ser Arg Ser Ala Asp Ala Pro Ala Tyr
        435                 440                 445

Gln Gln Gly Gln Asn Gln Leu Tyr Asn Glu Leu Asn Leu Gly Arg Arg
    450                 455                 460

Glu Glu Tyr Asp Val Leu Asp Lys Arg Arg Gly Arg Asp Pro Glu Met
465                 470                 475                 480

Gly Gly Lys Pro Arg Arg Lys Asn Pro Gln Glu Gly Leu Tyr Asn Glu
                485                 490                 495

Leu Gln Lys Asp Lys Met Ala Glu Ala Tyr Ser Glu Ile Gly Met Lys
            500                 505                 510

Gly Glu Arg Arg Arg Gly Lys Gly His Asp Gly Leu Tyr Gln Gly Leu
        515                 520                 525
```

Ser Thr Ala Thr Lys Asp Thr Tyr Asp Ala Leu His Met Gln Ala Leu
            530                 535                 540

Pro Pro Arg
545

<210> SEQ ID NO 22
<211> LENGTH: 415
<212> TYPE: PRT
<213> ORGANISM: Artificial Sequence
<220> FEATURE:
<223> OTHER INFORMATION: Synthetic Construct: Signal peptide - BAFF
      partial - linker - IgG1 hinge - CD28 transmb - CD28 and OX40
      signalling - CD3 zeta signalling

<400> SEQUENCE: 22

Met Glu Thr Asp Thr Leu Leu Leu Trp Val Leu Leu Trp Val Pro
1               5                   10                  15

Gly Ser Thr Gly Ala Val Gln Gly Pro Glu Glu Thr Val Thr Gln Asp
                20                  25                  30

Cys Leu Gln Leu Ile Ala Asp Ser Glu Thr Pro Thr Ile Gln Lys Gly
                35                  40                  45

Ser Tyr Thr Phe Val Pro Trp Leu Leu Ser Phe Lys Arg Gly Ser Ala
50                  55                  60

Leu Glu Glu Lys Glu Asn Lys Ile Leu Val Lys Glu Thr Gly Tyr Phe
65                  70                  75                  80

Phe Ile Tyr Gly Gln Val Leu Tyr Thr Asp Lys Thr Tyr Ala Met Gly
                85                  90                  95

His Leu Ile Gln Arg Lys Lys Val His Val Phe Gly Asp Glu Leu Ser
                100                 105                 110

Leu Val Thr Leu Phe Arg Cys Ile Gln Asn Met Pro Glu Thr Leu Pro
                115                 120                 125

Asn Asn Ser Cys Tyr Ser Ala Gly Ile Ala Lys Leu Glu Glu Gly Asp
130                 135                 140

Glu Leu Gln Leu Ala Ile Pro Arg Glu Asn Ala Gln Ile Ser Leu Asp
145                 150                 155                 160

Gly Asp Val Thr Phe Phe Gly Ala Leu Lys Leu Leu Ser Gly Gly Gly
                165                 170                 175

Ser Asp Pro Ala Glu Pro Lys Ser Pro Asp Lys Thr His Thr Cys Pro
                180                 185                 190

Pro Cys Pro Lys Asp Pro Lys Phe Trp Val Leu Val Val Val Gly Gly
                195                 200                 205

Val Leu Ala Cys Tyr Ser Leu Leu Val Thr Val Ala Phe Ile Ile Phe
210                 215                 220

Trp Val Arg Ser Lys Arg Ser Arg Leu Leu His Ser Asp Tyr Met Asn
225                 230                 235                 240

Met Thr Pro Arg Arg Pro Gly Pro Thr Arg Lys His Tyr Gln Pro Tyr
                245                 250                 255

Ala Pro Pro Arg Asp Phe Ala Ala Tyr Arg Ser Arg Asp Gln Arg Leu
                260                 265                 270

Pro Pro Asp Ala His Lys Pro Pro Gly Gly Gly Ser Phe Arg Thr Pro
                275                 280                 285

Ile Gln Glu Glu Gln Ala Asp Ala His Ser Thr Leu Ala Lys Ile Arg
                290                 295                 300

Val Lys Phe Ser Arg Ser Ala Asp Ala Pro Ala Tyr Gln Gln Gly Gln
305                 310                 315                 320

```
Asn Gln Leu Tyr Asn Glu Leu Asn Leu Gly Arg Arg Glu Glu Tyr Asp
                325                 330                 335

Val Leu Asp Lys Arg Arg Gly Arg Asp Pro Glu Met Gly Gly Lys Pro
            340                 345                 350

Arg Arg Lys Asn Pro Gln Glu Gly Leu Tyr Asn Glu Leu Gln Lys Asp
        355                 360                 365

Lys Met Ala Glu Ala Tyr Ser Glu Ile Gly Met Lys Gly Glu Arg Arg
370                 375                 380

Arg Gly Lys Gly His Asp Gly Leu Tyr Gln Gly Leu Ser Thr Ala Thr
385                 390                 395                 400

Lys Asp Thr Tyr Asp Ala Leu His Met Gln Ala Leu Pro Pro Arg
                405                 410                 415

<210> SEQ ID NO 23
<211> LENGTH: 416
<212> TYPE: PRT
<213> ORGANISM: Artificial Sequence
<220> FEATURE:
<223> OTHER INFORMATION: Synthetic Construct: alternaitive signal
      peptide - BAFF partial - linker - IgG1 hinge - CD28 transmb - CD28
      and OX40 signalling - CD3 zeta signalling

<400> SEQUENCE: 23

Met Ala Leu Pro Val Thr Ala Leu Leu Leu Pro Leu Ala Leu Leu Leu
1               5                   10                  15

His Ala Ala Arg Pro Ala Val Gln Gly Pro Glu Glu Thr Val Thr Gln
                20                  25                  30

Asp Cys Leu Gln Leu Ile Ala Asp Ser Glu Thr Pro Thr Ile Gln Lys
            35                  40                  45

Gly Ser Tyr Thr Phe Val Pro Trp Leu Leu Ser Phe Lys Arg Gly Ser
        50                  55                  60

Ala Leu Glu Glu Lys Glu Asn Lys Ile Leu Val Lys Glu Thr Gly Tyr
65                  70                  75                  80

Phe Phe Ile Tyr Gly Gln Val Leu Tyr Thr Asp Lys Thr Tyr Ala Met
                85                  90                  95

Gly His Leu Ile Gln Arg Lys Lys Val His Val Phe Gly Asp Glu Leu
            100                 105                 110

Ser Leu Val Thr Leu Phe Arg Cys Ile Gln Asn Met Pro Glu Thr Leu
        115                 120                 125

Pro Asn Asn Ser Cys Tyr Ser Ala Gly Ile Ala Lys Leu Glu Glu Gly
    130                 135                 140

Asp Glu Leu Gln Leu Ala Ile Pro Arg Glu Asn Ala Gln Ile Ser Leu
145                 150                 155                 160

Asp Gly Asp Val Thr Phe Phe Gly Ala Leu Lys Leu Leu Ser Gly Gly
                165                 170                 175

Gly Ser Asp Pro Ala Glu Pro Lys Ser Pro Asp Lys Thr His Thr Cys
            180                 185                 190

Pro Pro Cys Pro Lys Asp Pro Lys Phe Trp Val Leu Val Val Val Gly
        195                 200                 205

Gly Val Leu Ala Cys Tyr Ser Leu Leu Val Thr Val Ala Phe Ile Ile
    210                 215                 220

Phe Trp Val Arg Ser Lys Arg Ser Arg Leu Leu His Ser Asp Tyr Met
225                 230                 235                 240

Asn Met Thr Pro Arg Arg Pro Gly Pro Thr Arg Lys His Tyr Gln Pro
                245                 250                 255

Tyr Ala Pro Pro Arg Asp Phe Ala Ala Tyr Arg Ser Arg Asp Gln Arg
```

-continued

```
                    260                 265                 270
Leu Pro Pro Asp Ala His Lys Pro Pro Gly Gly Gly Ser Phe Arg Thr
        275                 280                 285

Pro Ile Gln Glu Glu Gln Ala Asp Ala His Ser Thr Leu Ala Lys Ile
        290                 295                 300

Arg Val Lys Phe Ser Arg Ser Ala Asp Ala Pro Ala Tyr Gln Gln Gly
305                 310                 315                 320

Gln Asn Gln Leu Tyr Asn Glu Leu Asn Leu Gly Arg Arg Glu Glu Tyr
                325                 330                 335

Asp Val Leu Asp Lys Arg Arg Gly Arg Asp Pro Glu Met Gly Gly Lys
                340                 345                 350

Pro Arg Arg Lys Asn Pro Gln Glu Gly Leu Tyr Asn Glu Leu Gln Lys
        355                 360                 365

Asp Lys Met Ala Glu Ala Tyr Ser Glu Ile Gly Met Lys Gly Glu Arg
        370                 375                 380

Arg Arg Gly Lys Gly His Asp Gly Leu Tyr Gln Gly Leu Ser Thr Ala
385                 390                 395                 400

Thr Lys Asp Thr Tyr Asp Ala Leu His Met Gln Ala Leu Pro Pro Arg
                405                 410                 415
```